United States Patent
Ozcan et al.

(10) Patent No.: US 11,501,544 B2
(45) Date of Patent: Nov. 15, 2022

(54) DEEP LEARNING-ENABLED PORTABLE IMAGING FLOW CYTOMETER FOR LABEL-FREE ANALYSIS OF WATER SAMPLES

(71) Applicant: THE REGENTS OF THE UNIVERSITY OF CALIFORNIA, Oakland, CA (US)

(72) Inventors: Aydogan Ozcan, Los Angeles, CA (US); Zoltan Gorocs, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 30 days.

(21) Appl. No.: 15/734,225

(22) PCT Filed: Jun. 4, 2019

(86) PCT No.: PCT/US2019/035376
§ 371 (c)(1),
(2) Date: Dec. 2, 2020

(87) PCT Pub. No.: WO2019/236569
PCT Pub. Date: Dec. 12, 2019

(65) Prior Publication Data
US 2021/0209337 A1    Jul. 8, 2021

Related U.S. Application Data

(60) Provisional application No. 62/680,374, filed on Jun. 4, 2018.

(51) Int. Cl.
*G06V 20/69* (2022.01)
*G06T 7/215* (2017.01)
(Continued)

(52) U.S. Cl.
CPC ...... *G06V 20/698* (2022.01); *B01L 3/502715* (2013.01); *G01N 15/147* (2013.01);
(Continued)

(58) Field of Classification Search
CPC ....... G06V 20/698; G06T 7/215; G06T 7/254; G06T 7/0012; G06T 2207/10024;
(Continued)

(56) References Cited

U.S. PATENT DOCUMENTS

| 2008/0292555 A1* | 11/2008 | Ye | G01N 15/1459 424/9.6 |
| 2012/0148141 A1* | 6/2012 | Ozcan | G01N 15/1434 382/133 |

(Continued)

FOREIGN PATENT DOCUMENTS

| EP | 2985719 A1 | 2/2016 |
| WO | 2011/049965 A1 | 4/2011 |

OTHER PUBLICATIONS

PCT International Preliminary Report on Patentability (Chapter I of the Patent Cooperation Treaty) for PCT/US2019/035376, Applicant: The Regents of the University of California, Form PCT/IB/326 and 373, dated Dec. 17, 2020 (12 pages).

(Continued)

*Primary Examiner* — Allen C Wong
(74) *Attorney, Agent, or Firm* — Vista IP Law Group LLP

(57) ABSTRACT

An imaging flow cytometer device includes a housing holding a multi-color illumination source configured for pulsed or continuous wave operation. A microfluidic channel is disposed in the housing and is fluidically coupled to a source of fluid containing objects that flow through the microfluidic channel. A color image sensor is disposed adjacent to the microfluidic channel and receives light from the illumination source that passes through the microfluidic (Continued)

channel. The image sensor captures image frames containing raw hologram images of the moving objects passing through the microfluidic channel. The image frames are subject to image processing to reconstruct phase and/or intensity images of the moving objects for each color. The reconstructed phase and/or intensity images are then input to a trained deep neural network that outputs a phase recovered image of the moving objects. The trained deep neural network may also be trained to classify object types.

22 Claims, 19 Drawing Sheets

(51) Int. Cl.
| | |
|---|---|
| G06T 7/254 | (2017.01) |
| B01L 3/00 | (2006.01) |
| G01N 15/14 | (2006.01) |
| G03H 1/00 | (2006.01) |
| G03H 1/04 | (2006.01) |
| G06K 9/62 | (2022.01) |
| G06T 7/00 | (2017.01) |
| H04N 5/225 | (2006.01) |
| G01N 15/10 | (2006.01) |

(52) U.S. Cl.
CPC ..... *G01N 15/1434* (2013.01); *G01N 15/1475* (2013.01); *G03H 1/0005* (2013.01); *G03H 1/0443* (2013.01); *G03H 1/0465* (2013.01); *G06K 9/6256* (2013.01); *G06T 7/0012* (2013.01); *G06T 7/215* (2017.01); *G06T 7/254* (2017.01); *H04N 5/2256* (2013.01); *B01L 2300/0663* (2013.01); *G01N 2015/1006* (2013.01); *G01N 2015/1454* (2013.01); *G03H 2001/0033* (2013.01); *G03H 2001/0445* (2013.01); *G03H 2210/55* (2013.01); *G03H 2210/62* (2013.01); *G03H 2222/13* (2013.01); *G03H 2222/16* (2013.01); *G03H 2222/34* (2013.01); *G03H 2223/15* (2013.01); *G03H 2223/24* (2013.01); *G06T 2207/10024* (2013.01); *G06T 2207/10028* (2013.01); *G06T 2207/10056* (2013.01); *G06T 2207/20084* (2013.01); *G06T 2207/30242* (2013.01)

(58) Field of Classification Search
CPC . G06T 2207/10028; G06T 2207/10056; G06T 2207/20084; G06T 2207/30242; B01L 3/502715; B01L 2300/0663; G01N 15/1434; G01N 15/147; G01N 15/1475; G01N 2015/1006; G01N 2015/1454; G06K 9/6256; H04N 5/2256; G03H 1/0005; G03H 1/0443; G03H 1/0465; G03H 2001/0033; G03H 2001/0445; G03H 2210/55; G03H 2210/62; G03H 2222/13; G03H 2222/16; G03H 2222/34; G03H 2223/15; G03H 2223/24
USPC .......................................................... 348/80
See application file for complete search history.

(56) References Cited

U.S. PATENT DOCUMENTS

| | | | |
|---|---|---|---|
| 2012/0157160 A1 | 6/2012 | Ozcan et al. | |
| 2012/0218379 A1 | 8/2012 | Ozcan et al. | |
| 2012/0248292 A1 | 10/2012 | Ozcan et al. | |
| 2012/0281899 A1 | 11/2012 | Ozcan et al. | |
| 2013/0092821 A1 | 4/2013 | Ozcan et al. | |
| 2013/0126618 A1* | 5/2013 | Gao | G06K 7/12 235/469 |
| 2013/0157351 A1* | 6/2013 | Ozcan | G01N 21/6486 422/69 |
| 2013/0193544 A1 | 8/2013 | Ozcan et al. | |
| 2013/0203043 A1 | 8/2013 | Ozcan et al. | |
| 2013/0258091 A1 | 10/2013 | Ozcan et al. | |
| 2013/0280752 A1 | 10/2013 | Ozcan et al. | |
| 2014/0120563 A1 | 5/2014 | Ozcan et al. | |
| 2014/0160236 A1 | 6/2014 | Ozcan et al. | |
| 2014/0192405 A1* | 7/2014 | Jaffe | G02B 27/30 359/379 |
| 2014/0226059 A1* | 8/2014 | Momose | H04N 5/2354 348/370 |
| 2014/0300696 A1 | 10/2014 | Ozcan et al. | |
| 2014/0355829 A1* | 12/2014 | Heu | G06V 10/22 382/103 |
| 2015/0111201 A1 | 4/2015 | Ozcan et al. | |
| 2015/0153558 A1 | 6/2015 | Ozcan et al. | |
| 2015/0204773 A1 | 7/2015 | Ozcan et al. | |
| 2016/0070092 A1 | 3/2016 | Ozcan et al. | |
| 2016/0161409 A1 | 6/2016 | Ozcan et al. | |
| 2016/0258859 A1* | 9/2016 | van den Engh | G01N 21/05 |
| 2016/0327473 A1 | 11/2016 | Ozcan et al. | |
| 2016/0334614 A1 | 11/2016 | Ozcan et al. | |
| 2017/0153106 A1 | 6/2017 | Ozcan et al. | |
| 2017/0160197 A1 | 6/2017 | Ozcan et al. | |
| 2017/0168285 A1 | 6/2017 | Ozcan et al. | |
| 2017/0220000 A1 | 8/2017 | Ozcan et al. | |
| 2017/0357083 A1 | 12/2017 | Ozcan et al. | |
| 2018/0003686 A1 | 1/2018 | Ozcan et al. | |
| 2018/0052425 A1 | 2/2018 | Ozcan et al. | |
| 2018/0299365 A1* | 10/2018 | Rieger | G01N 15/1434 |
| 2018/0373921 A1 | 12/2018 | Di Carlo et al. | |
| 2019/0119737 A1 | 4/2019 | Di Carlo et al. | |
| 2019/0137932 A1 | 5/2019 | Ozcan et al. | |
| 2019/0286053 A1 | 9/2019 | Ozcan et al. | |
| 2019/0294108 A1 | 9/2019 | Ozcan et al. | |
| 2019/0316172 A1 | 10/2019 | Ozcan et al. | |
| 2019/0333199 A1 | 10/2019 | Ozcan et al. | |
| 2019/0346369 A1 | 11/2019 | Ozcan et al. | |
| 2020/0103328 A1 | 4/2020 | Ozcan et al. | |
| 2020/0310100 A1 | 10/2020 | Ozcan et al. | |
| 2020/0340901 A1 | 10/2020 | Ozcan et al. | |

OTHER PUBLICATIONS

Bao, P. et al., Phase retrieval using multiple illumination wavelengths. Opt. Lett. 33, 309-311 (2008).
Bishara, W. et al., Lensfree on-chip microscopy over a wide field of-view using pixel super-resolution, May 24, 2010, vol. 18, No. 11, Optics Express, 11181-11191.
Bishara, W. et al., Holographic opto-fluidic microscopy, Dec. 20, 2010, vol. 18, No. 26, Optics Express, 27499-27510.
Bochdansky, A.B. et al., Development and Deployment of a Point-Source Digital Inline Holographic Microscope for the Study of Plankton and Particles to a Depth of 6000 m, Limnol. Oceanogr.: Methods 11, 2013, 28-40.
Dashkova, V. et al., Imaging flow cytometry for phytoplankton analysis. Methods 112, 188-200 (2017).
Faulkner, H.M. L. et al., Movable Aperture Lensless Transmission Microscopy: A Novel Phase Retrieval Algorithm, Physical Review Letter, vol. 93, No. 2, Jul. 9, 2004, 023903-1-023903-4.
Fienup, J.R. et al., Phase-retrieval stagnation problems and solutions, J. Opt. Soc. Am. A, vol. 3, No. I, Nov. 1986, 1897-1907.
Gérikas Ribeiro, C. et al., Estimating microbial populations by flowcytometry: Comparison between instruments, Limnology and Oceanography: Methods, Association for the Sciences of Limnology and Oceanography, 2017, 14(11), pp. 750-758. 10.1002/lom3. 10135. hal-01482199.
Göröcs, Z. et al., On-Chip Biomedical Imaging, IEEE Rev Biomed Eng. 2013 ; 6: 29-46. doi:10.1109/RBME.2012.2215847.
Greenbaum, A. et al., Maskless imaging of dense samples using pixel super-resolution based multi-height lensfree on-chip microscopy, Jan. 30, 2012, vol. 20, No. 3, Optics Express, 3129-3143.

(56) References Cited

OTHER PUBLICATIONS

Heflinger, L.O. et al., Holographic motion pictures of microscopic plankton. Appl. Opt. 17, 951-954 (1978).

Isikman, S.O. et al., Giga-Pixel Lensfree Holographic Microscopy and Tomography Using Color Image Sensors, PLOS ONE, www.plosone.org, Sep. 1, 2012, vol. 7, Issue 9, e45044.

Kiss, M.Z., et al., Special multicolor illumination and numerical tilt correction in volumetric digital holographic microscopy, Optic Express, Apr. 7, 2014, vol. 22, No. 7, 7559-7573, DOI:10.1364/OE.22.007559.

Leroux, R. et al., Combining laser diffraction, flow cytometry and optical microscopy to characterize a nanophytoplankton bloom in the Northwestern Mediterranean, Article in Progress In Oceanography, Oct. 2017, DOI: 10.1016/j.pocean.2017.10.010.

Luo, W. et al., Synthetic aperture-based on-chip microscopy, Light: Science & Applications (2015) 4, e261; doi:10.1038/lsa.2015.34.

Luo, W. et al., Pixel super-resolution using wavelength scanning, Light: Science & Applications (2016) 5, e16060 doi:10.1038/lsa.2016.60.

Olson, R.J. et al., A submersible imaging-in-flow instrument to analyze nano and microplankton: Imaging FlowCytobot, Limnol. Oceanogr.: Methods 5, 2007, 195-203.

Olson, R.J. et al., Imaging FlowCytobot modified for high throughput by in-line acoustic focusing of sample particles, Limnol. Oceanogr.: Methods 15, 2017, 867-874.

Pfitsch, D.W. et al., Development of a Free-Drifting Submersible Digital Holographic Imaging System, pp. 1-6 (2005).

Pomati, F. et al., An Automated Platform for Phytoplankton Ecology and Aquatic Ecosystem Monitoring, Environ. Sci. Technol. 2011, 45, 9658-9665, dx.doi.org/10.1021/es201934n.

Poulton, N. J., FlowCam: Quantification and Classification of Phytoplankton by Imaging Flow Cytometry. in Imaging Flow Cytometry 237-247 (Humana Press, New York, NY, 2016). doi: 10.1007/978-1-4939-3302-0_17).

Rivenson, Y. et al., Phase recovery and holographic image reconstruction using deep learning in neural networks, pp. 1-30 (2018).

Tamamitsu, M. et al., Comparison of Gini index and Tamura coefficient for holographic autofocusing based on the edge sparsity of the complex optical wavefront, pp. 1-9 (2017).

Taucher, J. et al., Influence of ocean acidification on plankton community structure during a winter-tosummer succession: An imaging approach indicates that copepods can benefit from elevated $CO_2$ via indirect food web effects, PLOS ONE, DOI:10.1371/journal.pone.0169737, Feb. 8, 2017, pp. 1-23.

Thyssen, M. et al., High-resolution analysis of a North Sea phytoplankton community structure based on in situ flow cytometry observations and potential implication for remote sensing, Biogeosciences, 12, 4051-4066, 2015.

Trask, B.J. et al., Analysis of Phytoplankton by Flow Cytometry, Cytometry, vol. 2, No. 4, 258-264 (1982).

Wu, Y. et al., Extended depth of field in holographic image reconstruction using deep learning based auto focusing and phase recovery, pp. 1-9 (2018).

Xu, W. et al., Digital in-line holography for biological applications, PNAS, Sep. 25, 2001, vol. 98, No. 20, 11301-11305.

Yourassowsky, C. et al., High throughput holographic imaging-in-flow for the analysis of a wide plankton size range, Optic Express, Mar. 24, 2014, vol. 22, No. 6, 6661-6673, DOI:10.1364/OE.22.006661.

Zetsche, E-M. et al., Imaging-in-Flow: Digital holographic microscopy as a novel tool to detect and classify nanoplanktonic organisms, Limnol. Oceanogr.: Methods 12, 2014, 757-775.

Zhang, Y. et al., Edge sparsity criterion for robust holographic autofocusing, Optics Letter, vol. 42, No. 19, Oct. 1, 2017, 3824-3827.

PCT International Search Report and Written Opinion for PCT/US2019/035376, Applicant: The Regents of the University of California, dated Oct. 15, 2019 (15 pages).

Response to the extended European search report dated Feb. 7, 2022 for European Patent Application No. 19815495.7-1001, Applicant: The Regents of the University of California, (75 pages).

The extended European search report dated Jul. 9, 2021 for European Patent Application No. 19815495.7-1001, Applicant: The Regents of the University of California, (11 pages).

Communication pursuant to Rules 70(2) and 70a(2) EPC dated Jul. 27, 2021, for European Patent Application No. 19815495.7-1001, Applicant: The Regents of the University of California, (1 page).

YoungJu Jo et al., Holographic deep learning for rapid optical screening of anthrax spores, bioRxiv, Feb. 16, 2017, XP055511774, DOI:10.1101/109108.

\* cited by examiner

FIG. 6

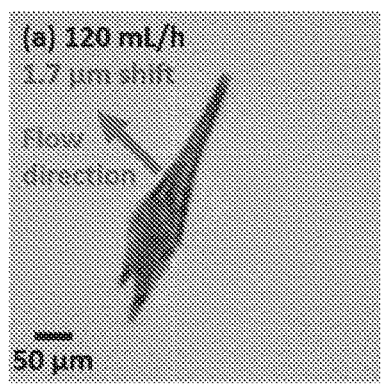 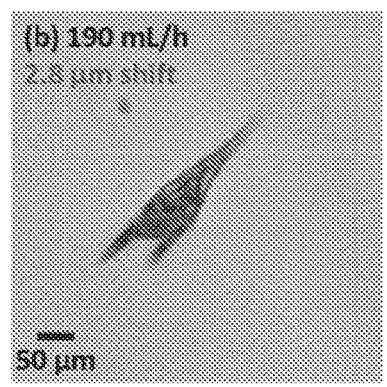
FIG. 14A    FIG. 14B
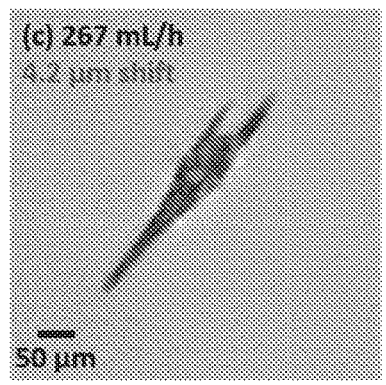 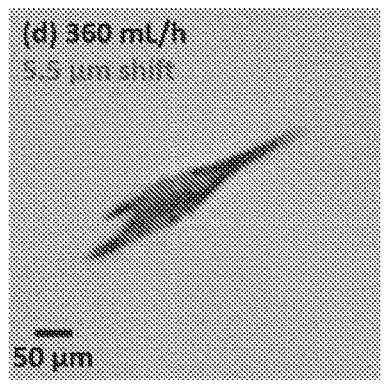 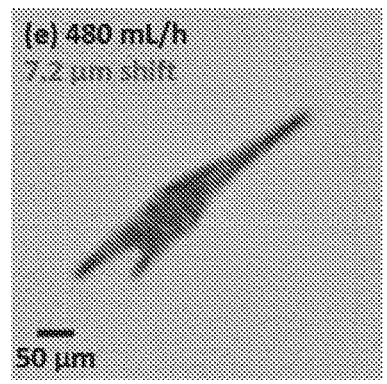
FIG. 14C    FIG. 14D    FIG. 14E
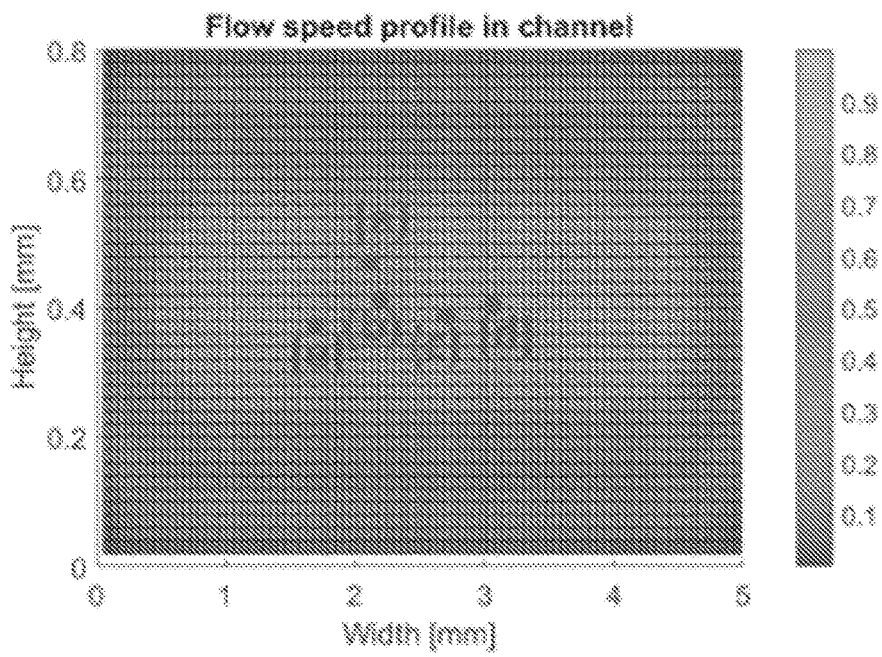
FIG. 14F

DEEP LEARNING-ENABLED PORTABLE IMAGING FLOW CYTOMETER FOR LABEL-FREE ANALYSIS OF WATER SAMPLES

RELATED APPLICATION

This Application is a U.S. National Stage filing under 35 U.S.C. § 371 of International Application No. PCT/US2019/035376, filed Jun. 4, 2019, which claims priority to U.S. Provisional Patent Application No. 62/680,374 filed on Jun. 4, 2018, which is hereby incorporated by reference. Priority is claimed pursuant to 35 U.S.C. § 119 and any other applicable statute.

STATEMENT REGARDING FEDERALLY SPONSORED RESEARCH AND DEVELOPMENT

This invention was made with government support under Grant Number W56HZV-16-C-0122, awarded by the U.S. Department of Defense. The government has certain rights in the invention.

TECHNICAL FIELD

The technical field generally relates to field-portable and cost-effective imaging flow cytometers. More specifically, the technical field relates to a deep learning-enabled flow cytometer that automatically captures phase-contrast color images of the contents of a flowing water sample.

BACKGROUND

Plankton forms the base of the oceanic food chain, and thus, it is an important component of the whole marine ecosystem. Phytoplankton is responsible for approximately half of the photoautotrophic primary production on our planet. High-resolution mapping of the composition of phytoplankton over extended periods is very important, and yet rather challenging because the composition and relative population of different species rapidly change as a function of space and time. Furthermore, the factors governing the phytoplankton concentration and composition are not fully understood, and its population dynamics is chaotic. The changes in the seasonal bloom cycle can also have major environmental and economic effects. The vast majority of the phytoplankton species are not harmful, but some species produce neurotoxins that can enter the food chain, accumulate, and poison fish, mammals, and ultimately humans. Notable examples include *Karenia brevis* producing brevetoxin and causing neurotoxic shellfish poisoning, *Alexandrium fundyense* generating saxitoxin and causing paralytic shellfish poisoning, *Dynophysis acuminata* producing okadaic acid resulting in diarrhetic shellfish poisoning, and *Pseudo-nitzschia* forming domoic acid responsible for amnesiac shellfish poisoning, which can even lead to deaths. Currently, the monitoring of the concentrations of these species in coastal regions, including in California (USA), is usually performed by manual sample collection from coastal waters using plankton nets, followed by transportation of the sample to a central laboratory for light microscopy-based analysis, which is very tedious, slow and expensive, requiring several manual steps performed by professionals.

As an alternative to light microscopy-based analysis, flow cytometry has been used to analyze phytoplankton samples for over 35 years. The technique relies on using a sheath flow to confine the plankton sample to the focal point of an illuminating laser beam and measuring the forward and side scattering intensities of each individual object/particle inside the sample volume. To aid classification, it is usually coupled with a fluorescence readout to detect the autofluorescence of chlorophyll, phycocyanin, and phycoerythrin, found in algae and cyanobacteria. Several field-portable devices based on flow cytometry have been successfully used for analyzing nano- and picophytoplankton distributions in natural water samples. However, taxonomic identification based solely on scattering and fluorescence data is usually not feasible in flow cytometry, and thus, these devices are coupled with additional microscopic image analysis or they need to be enhanced with some form of imaging.

Consequently, imaging flow cytometry has become a widely used technique in which a microscope objective is used to image the sample (e.g., algae) within a fluidic flow. The image capture is triggered by a fluorescence detector, and thus, objects with a detectable autofluorescence are imaged. Some of the widely utilized and commercially available imaging flow cytometers include the Flowcam (Fluid Imaging Technologies), Imaging Flowcytobot (McLane Research Laboratories), and CytoSense (Cytobouy b.v.). Although these systems are able to perform imaging of the plankton in a flow, they still have some important limitations. The use of a microscope objective lens provides a strong trade-off mechanism between the image resolution and the volumetric throughput of these systems; therefore, for obtaining high-quality images, the measured sample volume is limited to a few mL per hour (e.g., 3-15 mL/h). Using lower magnification objective lenses can scale up this low throughput by~10 fold at the expense of the image quality. In addition, the shallow depth-of-field of the microscope objective necessitates hydrodynamic focusing of the liquid sample into a few μm-thick-layer using a stable sheath flow. This also restricts the size of the objects that can be imaged (e.g., to <150 μm) as well as the flow velocity and thereby the throughput of the system, which requires the use of additional expensive techniques such as acoustic focusing. As a result of these factors, currently existing imaging flow cytometers used in environmental microbiology field are fairly bulky (weighing e.g., 9-30 kg) and costly (>$40,000-$100,000), limiting their wide-spread use.

In contrast to some of these existing fluorescence-based approaches, holographic imaging of plankton samples provides a label-free alternative; in fact its use in environmental microbiology started over 40 years ago using photographic films and subsequently continued via digital cameras and reconstruction techniques. Holography provides a volumetric imaging technique that uses coherent or partially-coherent light to record the interference intensity pattern of an object. This hologram can subsequently be reconstructed to digitally bring the object into focus. The hologram contains information on the complex refractive index distribution of the object, and as such, not only the absorption but also the phase distribution of the sample can be retrieved. There are several implementations of digital holography for imaging a fluidic flow.

One can classify these digital holographic microscopy systems in terms of the presence of an external reference wave (in-line or off-axis), magnification of the imaged volume, and utilization of a lens or spherical wavefront for illumination. Off-axis systems can directly retrieve the phase information from the captured hologram; however, their space-bandwidth product and image quality are generally worse than those of in-line systems. Commercially-available on-line holographic imaging flow cytometer systems also exist, such as the LISST-Holo2 (Sequoia Scientific, Inc., Bellevue, Wash.). This platform is a monochrome system (i.e., does not provide color information) and offers a relatively poor image quality compared to traditional imaging flow cytometers. The throughput and spatial resolution are coupled in this device, and therefore it can achieve high throughput volumetric imaging at the cost of limited resolution (~25-2500 µm equivalent spherical diameter with 4 µm feature resolution) which makes it useful for detecting and identifying only larger organisms. Higher resolution and better image quality systems using microscope objectives in the optical path have also been described, however, the use of microscope objective lenses not only makes these systems more expensive, but also limits the achievable field-of-view (FOV) and depth-of-field, and therefore drastically reduces the throughput of the system e.g., ~0.8 mL/h.

SUMMARY

In one embodiment, a powerful and yet mobile and inexpensive imaging flow cytometer device is provided for environmental microbiology and related uses. An in-line holographic imaging flow cytometer is provided that is able to automatically detect and in real-time or near real-time provide color images of label-free objects inside a flowing water sample at a throughput of ~100 mL/h or higher. In one embodiment, the high-throughput imaging flow cytometer weighs approximately 1 kg with a size of around 15.5 cm×15 cm×12.5 cm. The imaging flow cytometer obtains images of objects in the flowing water sample based on a deep learning-enabled phase recovery and holographic reconstruction framework running on a computing device such as a laptop or the like that, in some embodiments, is also used to control the imaging flow cytometer device. Compared to other imaging flow cytometers, the imaging flow cytometer device is significantly more compact, lighter weight and extremely cost-effective, with parts costing less than $2,500 in total, which is only a fraction of the cost of existing imaging flow cytometers. This imaging flow cytometer device can continuously examine the liquid pumped through a 0.8-mm thick microfluidic chip without any fluorescence triggering or hydrodynamic focusing of the sample, thereby also making the device robust and very simple to operate, covering a very large dynamic range in terms of the object size, from microns to several hundreds of microns.

The imaging flow cytometer device may be used, in some embodiments, to image water-borne microorganisms. Waterborne microorganisms include micro-plankton and nanoplankton as well as algae. Other microorganism including parasites and the like may also be imaged with the imaging flow cytometer device. Examples of such water-borne parasites include, for example, *Giardia*. *Giardia* is a microscopic parasite that causes the diarrheal illness known as giardiasis. In other embodiments, the imaging flow cytometer device may be used to count or quantify the numbers of water-borne microorganisms in a sample. This includes the total number of water-borne microorganisms as well as identifying particular sub-counts of particular species or classes of microorganisms. In still other embodiments, the flow cytometer device is capable of classifying identified microorganism as belonging to a particular species, class, or phenotype.

The capabilities of the field-portable holographic imaging flow cytometer were demonstrated by imaging micro-plankton and nano-plankton composition of ocean samples along the Los Angeles coastline, and also measured the concentration of potentially harmful algae *Pseudo-nitzschia*, achieving a good agreement with independent measurements conducted by the California Department of Public Health (CDPH). Of course, other microorganisms may also be imaged as noted herein. These field results establish the effectiveness of the high-throughput imaging flow cytometer. The imaging flow cytometer device, in other embodiments, may form the basis of a network of a plurality of imaging flow cytometers that can be deployed for large-scale, continuous monitoring and quantification of microscopic composition of water samples. For example, environmental observers in the field may use the device to monitor the status or health of various water bodies. This may include oceans, rivers, lakes, streams, ponds, potable water sources, and the like.

In one embodiment, a portable imaging flow cytometer device is disclosed that includes a housing or enclosure that contains an illumination source comprising multiple color light emitting diodes (LEDs) configured for simultaneous, pulsed or continuous wave operation (the multiple color LEDs may exist on a single chip). The device also includes one or more bandpass filters configured to spectrally filter the light from the multiple color LEDs to adjust the coherence of the light that irradiates the fluid sample. The imaging flow cytometer device includes a microfluidic device that has a microfluidic channel fluidically coupled to a pump (also located in the housing or enclosure in one embodiment) that is configured to pump a water-based fluid through the microfluidic channel of the microfluidic device. A color image sensor is disposed adjacent to the microfluidic channel and is located along an optical path that contains the spectrally filtered light from the multiple color LEDs. The color image sensor is configured to capture image frames containing raw hologram images of objects (e.g., microorganisms) contained in the water passing through the microfluidic channel.

In one embodiment, the optical path from the light source to the color image sensor is a folded optical path. This advantageously reduces the overall size of the device. This may be accomplished using, in one embodiment, a mirror (e.g., a convex mirror) that is located in the housing or enclosure. Alternatively, the optical path is non-folded but this may result in a larger device size. The multiple color LEDs are powered, in one embodiment, in pulses by one or more capacitors that are charged using charging circuitry also contained in the device. The portable imaging flow cytometry device further includes or is associated with a computing device that is configured to receive the plurality of image frames generated by the color image sensor. The computing device may be formed separate from the housing or enclosure that holds the various components of the imaging flow cytometer device. This computing device may include a computer such as a laptop, personal computer, tablet PC, or the like that is co-located with the imaging flow cytometer device. Alternatively, or in addition to, a remote computer such as server or the like may be utilized for image processing. Preferably, the computing device uses a graphics processing unit (GPU) which is used for image processing to increase the processing speed of the imaging flow cytometer device so that it can generate real-time or near real-time results. The computing device includes image processing software contained therein (or executed thereby) that is configured to perform, among other operations, background subtraction and automatically detect objects in the acquired image frames. In one embodiment, the user of the imaging flow cytometer device interfaces with the image processing/control software using a graphical user interface (GUI).

The image processing software is also configured to reconstruct phase and/or intensity images of the detected objects for each LED color hologram that is acquired. In one particular embodiment, the reconstruction is performed using a wave propagation algorithm such as an angular-spectrum-based wave propagation algorithm to obtain both reconstructed phase images and intensity images for each color channel (six total images in all for a candidate object of interest). In a preferred embodiment, the image processing software further comprises a trained deep neural network that utilizes the reconstructed phase and/or intensity images as an input. The trained deep neural network then outputs a phase recovered phase and/or intensity images that, in one embodiment, are then digitally generated (e.g., merged) to create a phase-contrast image of the detected objects. In one alternative embodiment, the image processing software is configured to automatically characterize or identify the type of detected object. The image processing software may be implemented in any number of software programs or languages. Examples include, by way of illustration and not limitation, C/C++ and the CUDA Application Program Interface (API). The deep neural network may be implemented using the NVIDIA CUDA Deep Neural Network library (cuDNN) although the invention is not limited to this specific implementation.

In one embodiment, a method of imaging objects using the imaging flow cytometry device includes: obtaining a plurality of image frames of objects while fluid containing the objects is pumped or otherwise flowed through the microfluidic channel. A background subtraction operation is performed using the image processing software to remove artifacts dust, dirt, and the like. Potential objects of interest are then identified after background subtraction with the image processing software. Next, the image processing software reconstructs intensity and phase images of the objects. These reconstructed intensity and phase images of the objects, while improved in resolution compared to the holograms nonetheless have artifacts such as twin-image artifact. To address this, the reconstructed intensity and phase images of the objects are then input into a trained deep neural network executed by the image processing software, wherein the trained deep neural network outputs a phase recovered intensity and phase images of the objects. The phase recovered intensity and phase images of the objects can then be digitally generated or calculated (e.g., merged) to create a phase recovered phase-contrast image of the detected objects.

In another embodiment, the imaging flow cytometer device uses a monochrome image sensor and a corresponding light source which may include a single light source. For example, this configuration may be sufficient for object or particle counting or classification of objects that do not require the additional color information.

In another embodiment, a color image sensor is used in conjunction with a near-infrared (IR) light source. This may include a LED, laser diode, or other light source. In addition, in various embodiments, it may be possible to omit the one or more filters (this includes the monochrome embodiment as well as the color embodiment). For example, if more narrow-band imaging sources are used, the filters may be dispensed with entirely.

In one embodiment, the some or all of the objects may be identified prior to reconstruction (e.g., using the holograms themselves). In this embodiment, for example, only a smaller sub-set of objects may then be reconstructed as opposed to the entire image frame.

The imaging flow cytometer device requires a computing device for processing the acquired data (i.e., images) and/or control of the imaging flow cytometer device itself. This may take place using a local computing device that is connected to or integrated into the imaging flow cytometer device itself. For example, any number of local interfaces may be used including wired connections such as USB, GigE, Ethernet or the like. A wireless connection may also be used. In other embodiments, some aspects of the processing of acquired data and/or control of the imaging flow cytometer device may be divided between a local computing device and a remote computing device. For example, control of the operational parameters of the imaging flow cytometer device may be controlled using a local computing device while a remote computer (e.g., server) may be used for image processing.

In one embodiment, a portable imaging flow cytometer device is provided that includes a housing or enclosure. At least one illumination source is disposed in the housing or enclosure and configured for pulsed or continuous wave operation. A microfluidic channel (e.g., part of a microfluidic device) is disposed in the housing and is fluidically coupled to a source of fluid containing objects therein that is configured to flow through the microfluidic channel. An image sensor is disposed adjacent to the microfluidic channel and disposed within an optical path that receives light from the at least one illumination source that passes through the microfluidic channel, the image sensor configured to capture a plurality of image frames containing raw hologram images of the objects passing through the microfluidic channel.

The portable image flow cytometry device communicates with a computing device that has image processing software executed thereon or thereby which is configured to perform background subtraction and automatically detect moving objects (e.g., microorganisms) in the plurality of image frames. The image processing software is also configured to segment moving objects in the plurality of frames and autofocus the moving objects to identify the height (z) location of the moving objects within the microfluidic channel. In one embodiment, the image processing software is further configured to reconstruct phase and/or intensity images of the moving objects for each color (e.g., red, blue, green). For example, the reconstruction may be performed using an angular-spectrum-based wave propagation algorithm. The image processing software may further include a trained deep neural network, wherein the reconstructed phase and/or intensity images are input to the trained deep neural network that outputs a phase recovered intensity and/or phase image of the moving objects. Alternatively, or in addition to, the phase recovered intensity and phase images may be combined to generate a phase recovered phase-contrast image of the moving objects.

In another embodiment, a method of imaging objects using the flow cytometry device includes obtaining a plurality of image frames while fluid containing objects (e.g., microorganisms) is flowed through the microfluidic channel. A background subtraction operation is performed using image processing software to remove artifacts. Moving objects are identified in the plurality of image frames after background subtraction with the image processing software. Reconstructed intensity and phase images of the moving objects are generated using the image processing software. The reconstructed intensity and phase images of the moving objects are then input into a trained deep neural network executed by the image processing software, wherein the trained deep neural network outputs a phase recovered intensity and/or phase image of the moving objects or a phase recovered phase-contrast image of the moving objects.

In another embodiment, the trained deep neural network (used to output phase recovered images) is replaced with a trained neural network classifier that classifies observed moving objects into one or more object types. For example, the trained neural network classifier receives as inputs reconstructed intensity and phase images of the moving objects and then outputs a binary output of whether the object is a particular type or not (i.e., yes or no). For example, the trained neural network classifier may be used to classify microorganisms as a particular species or phenotype.

In another embodiment, a method of imaging objects using the flow cytometry device includes obtaining a plurality of image frames while fluid containing objects is flowed through the microfluidic channel and performing a background subtraction operation using image processing software to remove artifacts. Moving objects are identified in the plurality of image frames after the background subtraction with the image processing software. The image processing software is used to reconstruct intensity and phase images of the moving objects. The reconstructed intensity and phase images of the moving objects is then input into a trained deep neural network executed by the image processing software, wherein the trained deep neural network outputs a refractive index distribution inside the moving objects. Alternatively, or in addition to the refractive index distribution inside the moving objects, the trained deep neural network may output the thickness of the moving objects. In one particular embodiment, the refractive index distribution may be used as a proxy to measure composition of the microorganism (e.g., chemical or lipid content).

BRIEF DESCRIPTION OF THE DRAWINGS

FIG. 6 illustrates another example of the graphical user interface (GUI) that is used on the computing device (e.g., laptop computer) that is used in connection with the imaging flow cytometer device. The smaller images show different reconstructed images of objects detected in a single frame which have been cropped.

*Nitzschia* in the ocean. Samples were collected according to California Department of Public Health (CDPH) protocols. A part of each sample was analyzed by the imaging flow cytometer system, and the remaining part was sent to CDPH for subsequent analysis, which showed a good agreement to our measurements. Inset shows the phase-contrast reconstruction examples of *Pseudo-Nitzschia*, an alga which can produce domoic acid, a dangerous neurotoxin that causes amnesic shellfish poisoning.

Figure 13:
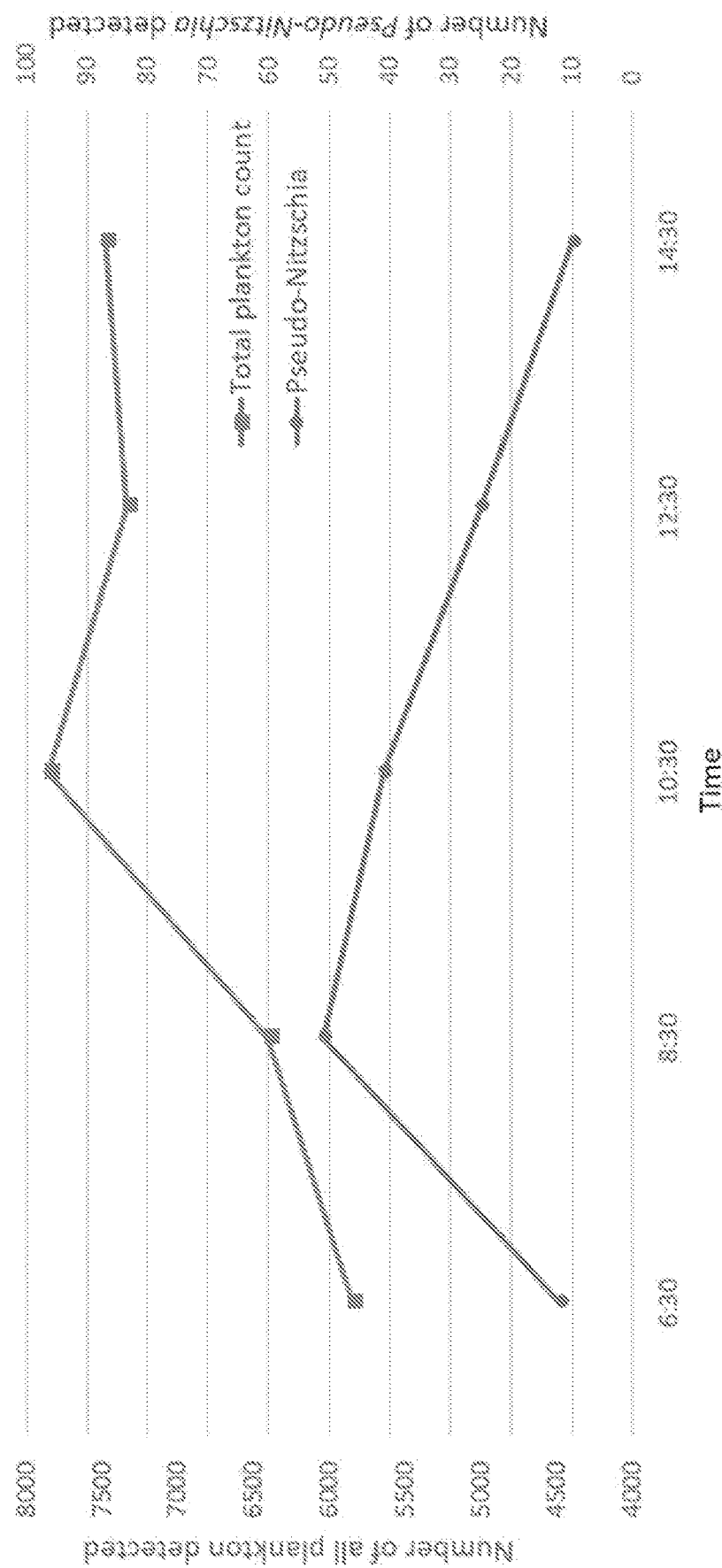

FIG. 13 illustrates a graph showing field test results from a series of measurements of ocean water obtained at Redondo Beach. The top 1.5 m of the ocean was sampled every 2 hours and on-site the variation in the plankton concentration was measured or observed over time. The measurement started after sunrise (6.21 AM), and each sample was imaged on-site using the flow cytometer. The results show an increase in the total plankton count during the day, whereas the number of *Pseudo-Nitzschia* shows a peak during the morning hours.

FIGS. 14A-14F illustrate the effect of increasing the liquid flow speed in the system on the image quality. The relative flow speed profile inside the rectangular channel cross-section is depicted in the top left (FIG. 14F). The measurements were made on an ocean sample containing a high concentration of *Ceratium Furca*, and thus, it was used as the model organism for this test. The sample was tested at various flow speeds above 100 mL/h while keeping the 120-µs-illumination pulse length constant. Objects located inside the channel near the maximum-flow velocity regions (generally central region) were chosen, and their locations are depicted as dots. FIGS. 14A-14E are reconstructed intensities corresponding to different flow rates. The flow rate (mL/h) and the theoretically calculated displacement (µm) during the illumination pulse are also shown.

Figure 15:
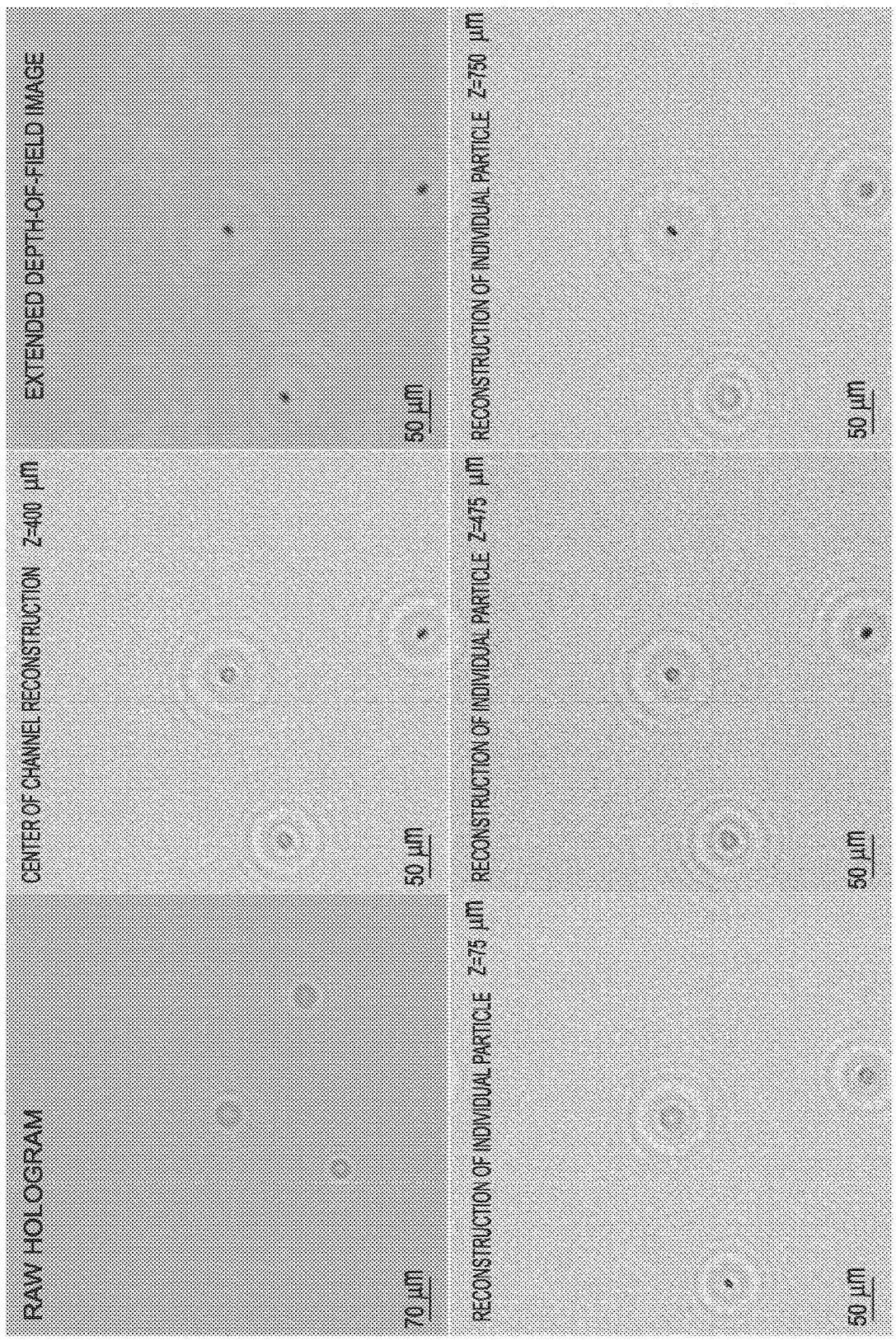

FIG. 15 illustrates deep learning-based extended depth-of-field (DOF) reconstruction of flowing *Giardia* cysts. (Top row) The raw hologram captured by the image sensor is separated into individual color channels and reconstructed at the height, approximately corresponding to the center of the channel. This initial reconstruction is used as an input for a deep neural network trained to reconstruct holograms irrespective of their object heights in a single step, automatically implementing the function of both auto-focusing and phase recovery; thereby generating an extended depth-of-field image of the scene by simultaneously reconstructing all the particles' image in focus. (Bottom row) Individual reconstructions of the same raw hologram using autofocusing on each particle. Particles reconstruct at different heights spanning the height of the flow channel (0-800 µm); this comparison between the top and bottom rows clearly shows that the whole volume can be coalesced into a single plane using a deep neural network based extended DOF reconstruction (top right image), enabling the reconstruction of dense water samples without being bottlenecked with the local computational power that is available.

Figure 16:
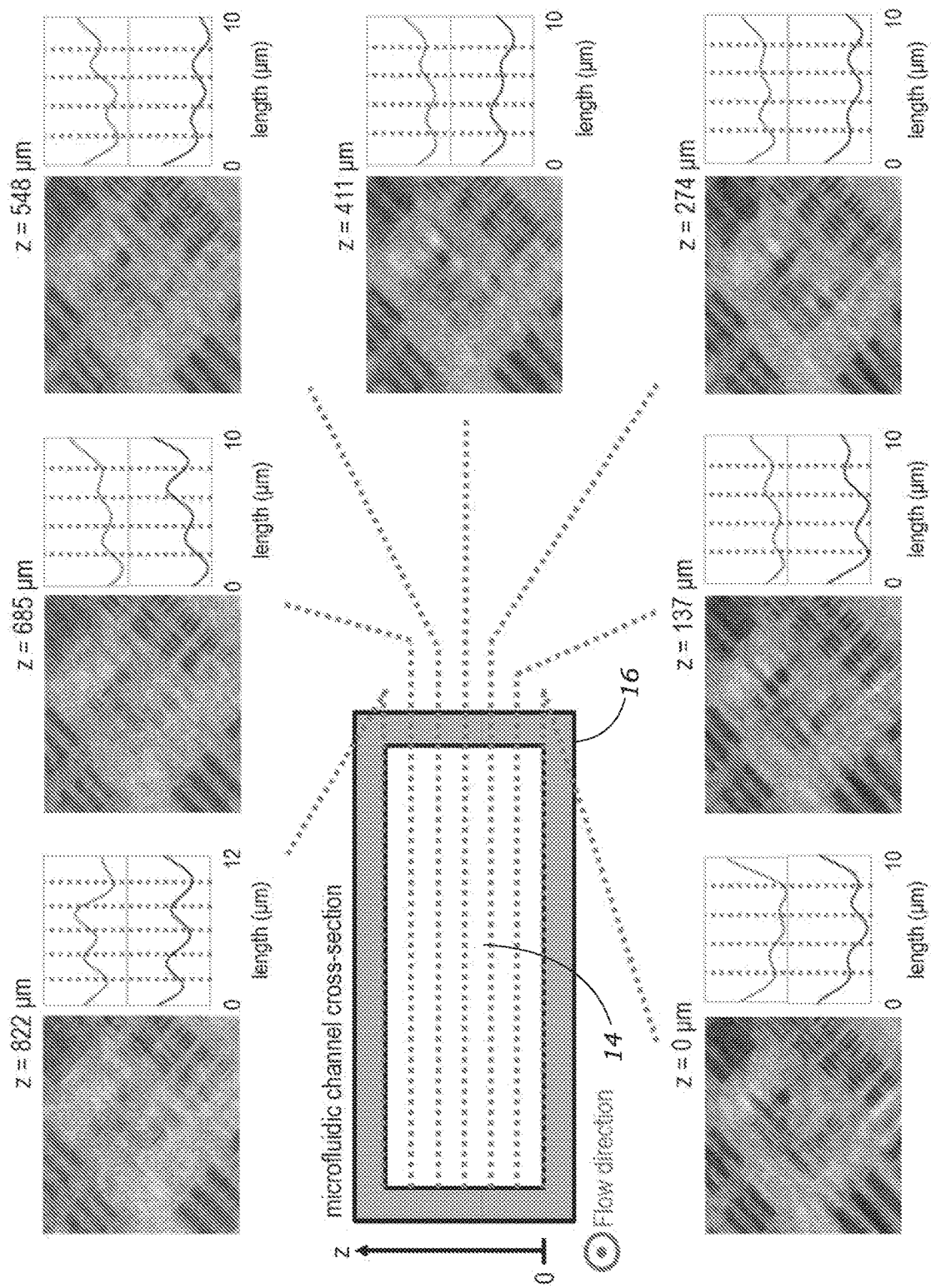

FIG. 16 illustrates the imaging performance of the imaging flow cytometer device. A 1951 Air Force test chart was placed at seven different distances (z) from the CMOS sensor plane corresponding to the height range of the microfluidic channel. The smallest resolved element on the chart up to ~550 µm height is group 8 element 3, corresponding to a linewidth of 1.55 µm. Above this height, the coherence of the light reduces the achievable resolution steadily with z distance, with the top of the channel resolving a linewidth of 1.95 µm corresponding to group 8 element 1.

Figure 17A:
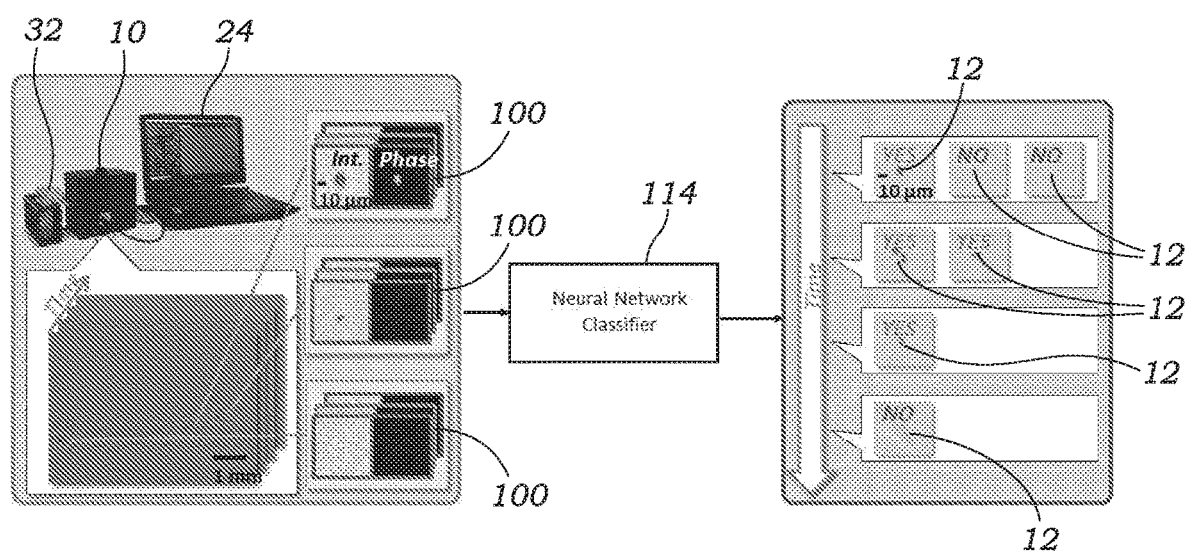

FIG. 17A schematically illustrates the flow cytometry imaging system that is used in conjunction with a neural network classifier that is trained on the reconstructed images to detect and count specific microorganisms.

Figure 17B:
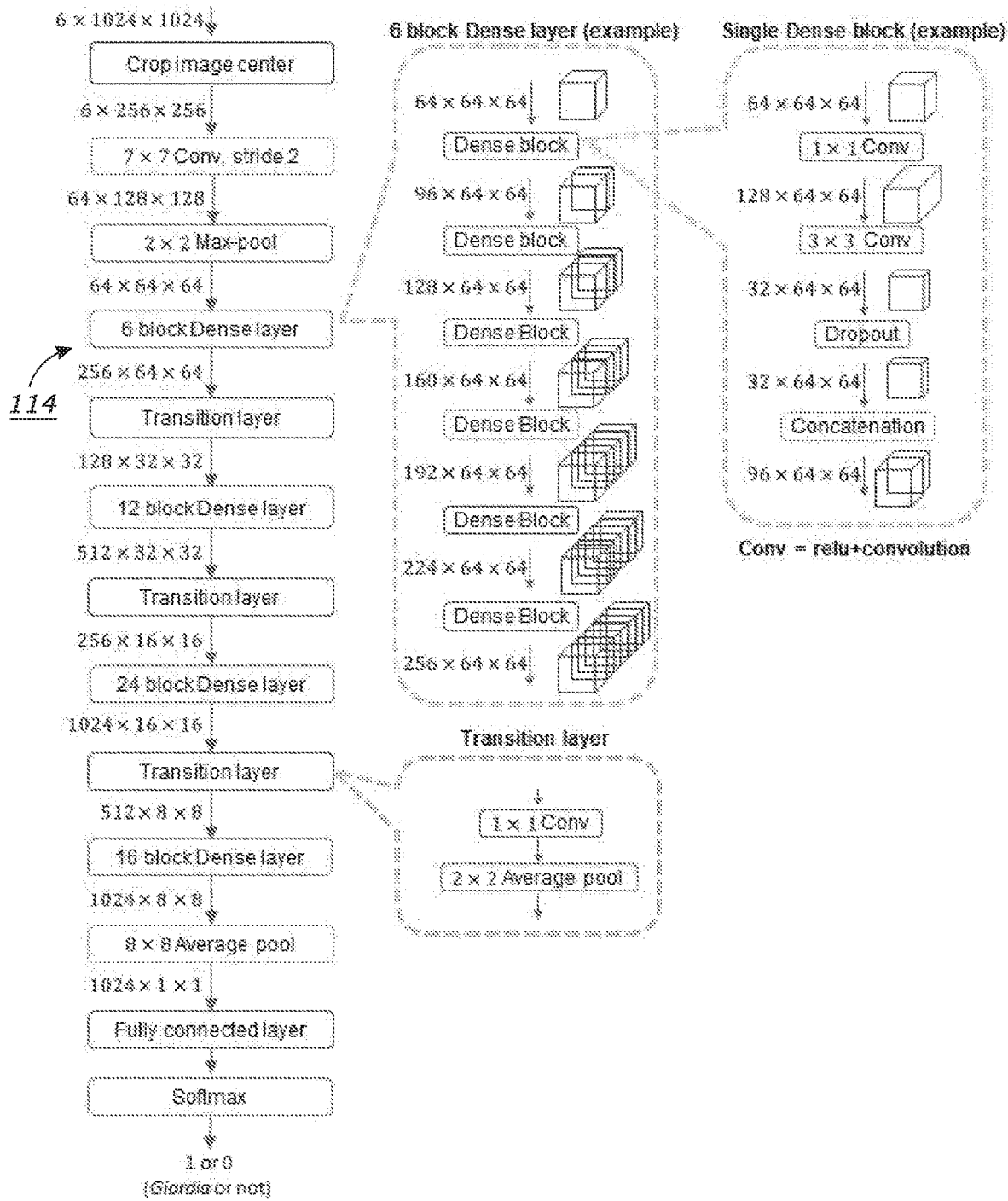

FIG. 17B illustrates the details of the DenseNet neural network classifier network according to one embodiment.

Figure 18:
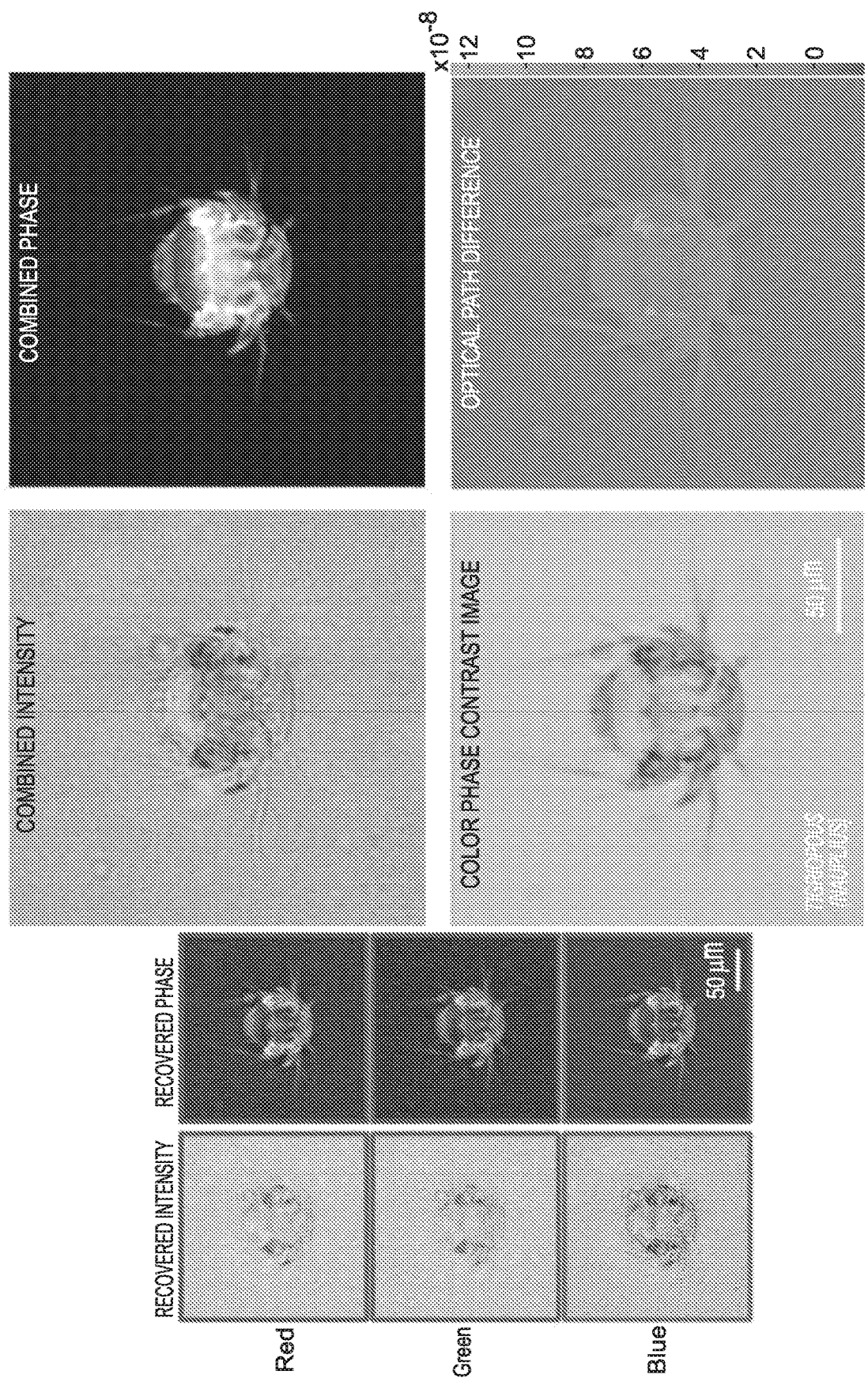

FIG. 18 illustrates an example of optical path length difference measurement made using the imaging flow cytometer device. For each object in the field of view the cytometer device obtains not just the intensity but also the phase information in each of the red, green, and blue color channels (shown by the corresponding frame color). Transparent parts of plankton (*Tigriopus nauplii*) are not visible in the conventional bright field (combined intensity) color image, but due to the mismatch of refractive index between the exoskeleton and the surrounding water, it becomes visible in phase (combined phase). For visualization a phase contrast image can be generated to fuse the intensity and phase to get a high contrast color image of the object. Similarly, the optical path length difference can be computed which contains information of the thickness and refractive index distribution of the object (optical path difference image—lower right).

DETAILED DESCRIPTION OF ILLUSTRATED EMBODIMENTS

Figure 1:
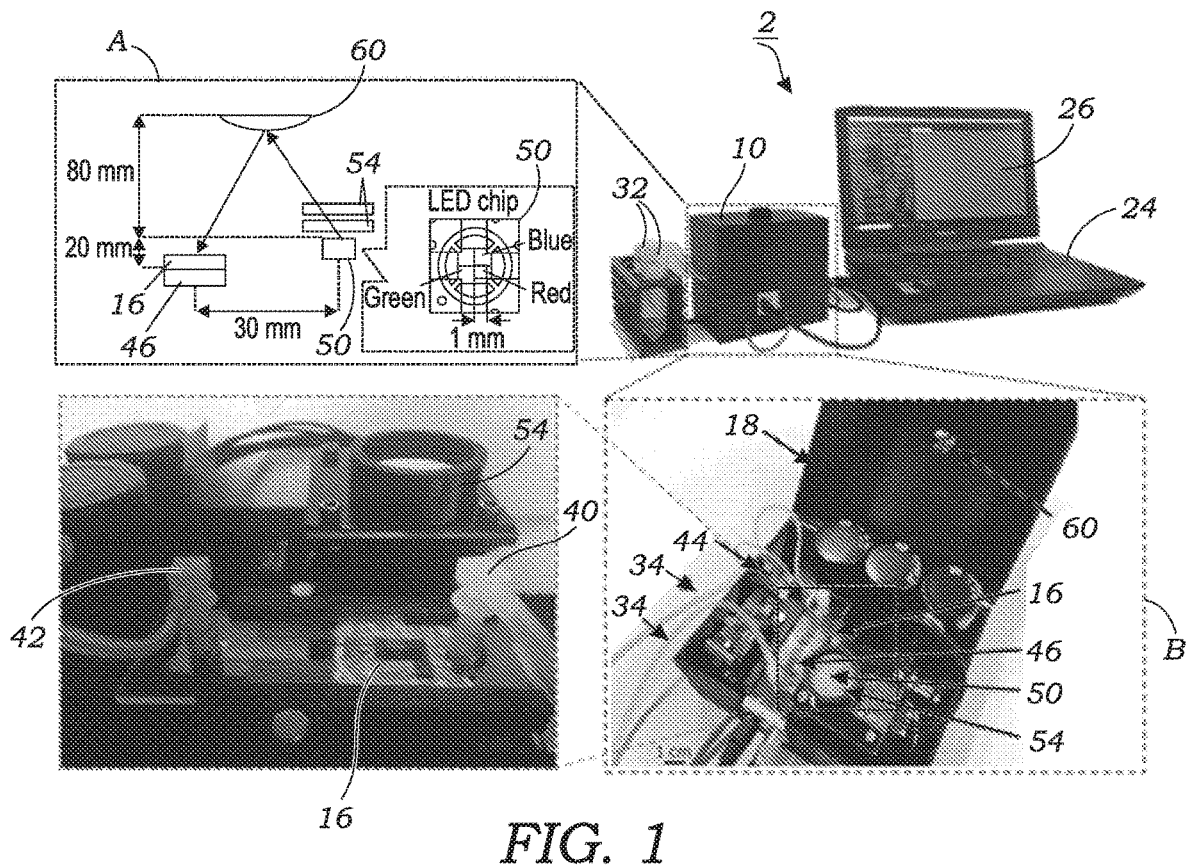
FIG. 1 illustrates a photograph of the flow cytometry imaging system that includes an imaging flow cytometer device, source of sample-containing fluid, and a computing device. Also illustrated in panel A is a schematic representation of the microfluidic channel and imaging sub-systems of the flow cytometer device. Panel B illustrates a photographic image the housing or enclosure of the imaging flow cytometer device in the open state showing various components. To the side of panel B is a photographic image of the dashed region of Panel B showing the microfluidic device having the microfluidic channel. Also seen in the illumination source and filters.
Figure 3:
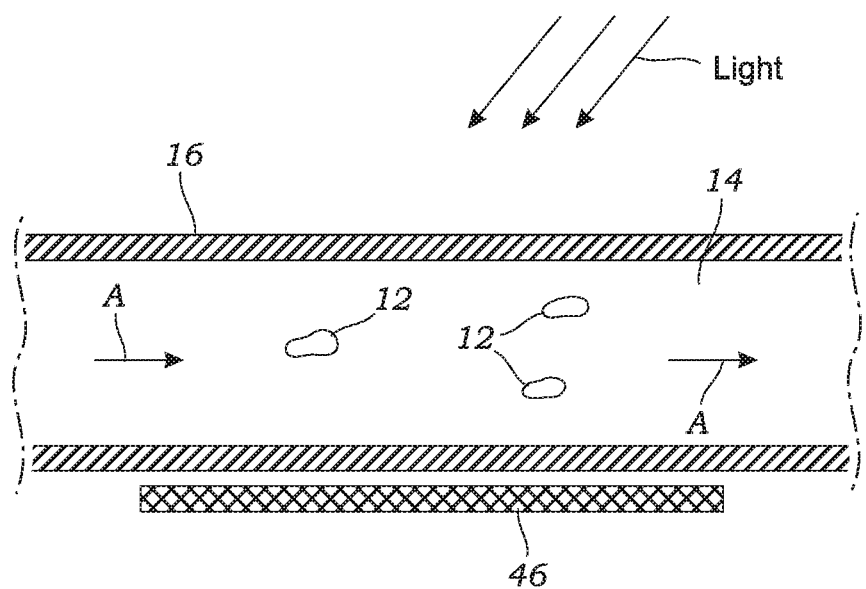
FIG. 3 illustrates a cross-sectional view of the microfluidic channel illustrating moving objects flowing through the microfluidic channel (in the directions of arrows A).
Figure 4A:
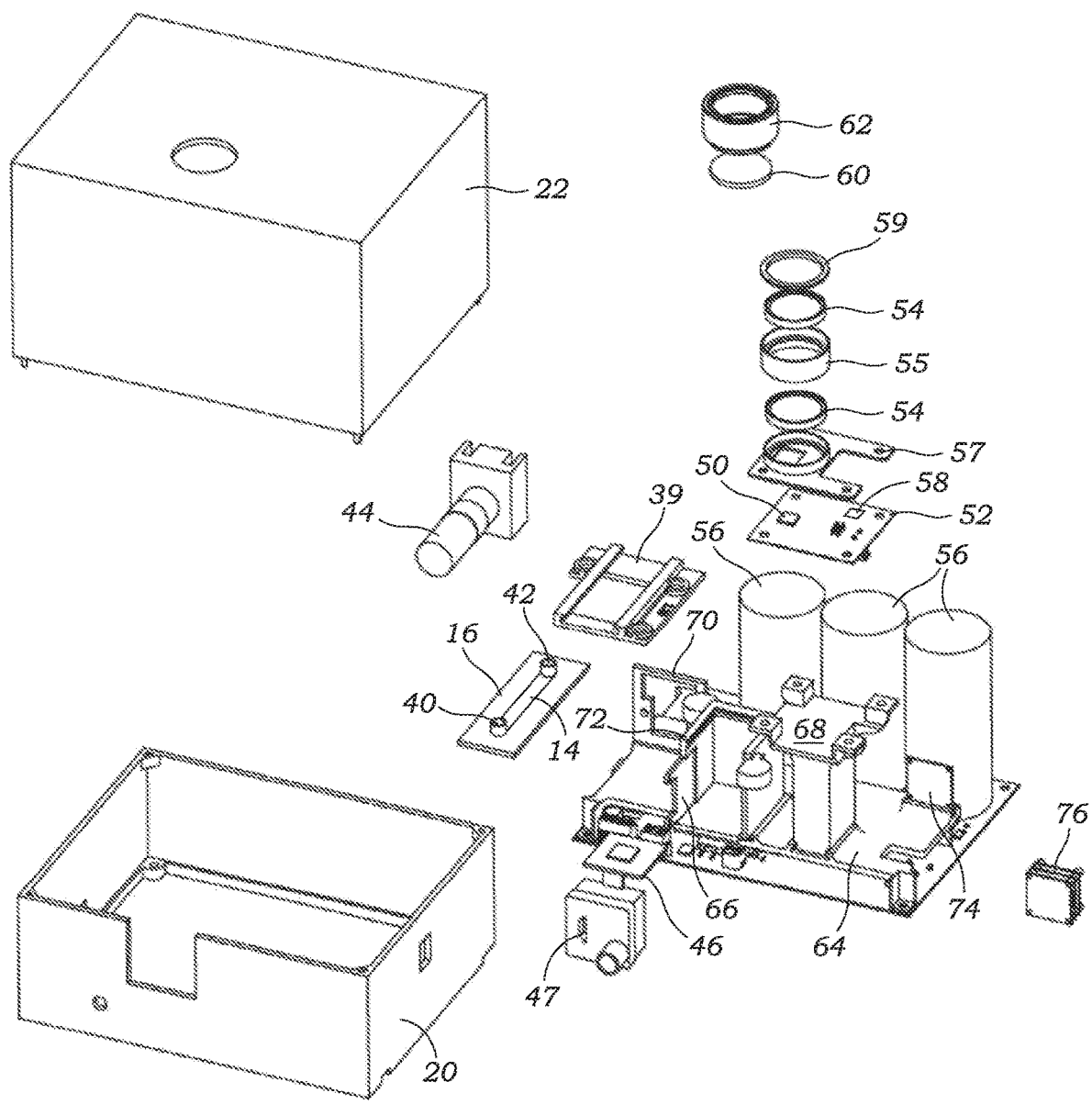
FIG. 4A illustrates an exploded view of the components of the imaging flow cytometer device according to one embodiment.

FIG. 1 illustrates photographic image of a flow cytometry imaging system 2 that incorporates an imaging flow cytometer device 10 that, in one embodiment, obtains images of moving objects 12 such as those seen in FIG. 3 moving in the direction of arrows A that pass through a microfluidic channel 14 of a microfluidic device 16. The moving objects 12 are carried within a flowing fluid within the microfluidic channel 14. The flowing fluid is typically an aqueous-based fluid such as water. FIG. 1 also illustrates (in image panel A) a schematic view of various internal components of the imaging flow cytometer device 10. Image panel B shows a photographic view of the internal working components of the imaging flow cytometer device 10 with a housing or enclosure 18 in an open state. The housing or enclosure 18 may include a bottom portion 20 as best seen in FIG. 4A that contains the majority of the components of the imaging flow cytometer device 10. The housing 18 may include a lid or top 22 that, in one embodiment, is hinged or connected to the bottom portion 20 and may be opened/closed to provide access to the internal portion of the housing 18. The overall size of the imaging flow cytometer device 10 which is contained within the housing or enclosure 18 is small enough such that the imaging flow cytometer device 10 is portable and can be moved from location to location. In one embodiment, the imaging flow cytometer device 10 weighs around 1 kg or less and has total volume that is less than about 3,000 cm$^3$. For example, the imaging flow cytometer device 10 may have dimensions of around 15.5 cm×15 cm×12.5 cm as an example. Compared to other imaging flow cytometers, the imaging flow cytometer device 10 is significantly more compact, lighter weight and extremely cost-effective, with its parts costing less than $2,500, which is only a fraction of the cost of existing imaging flow cytometers.

Figure 9A:
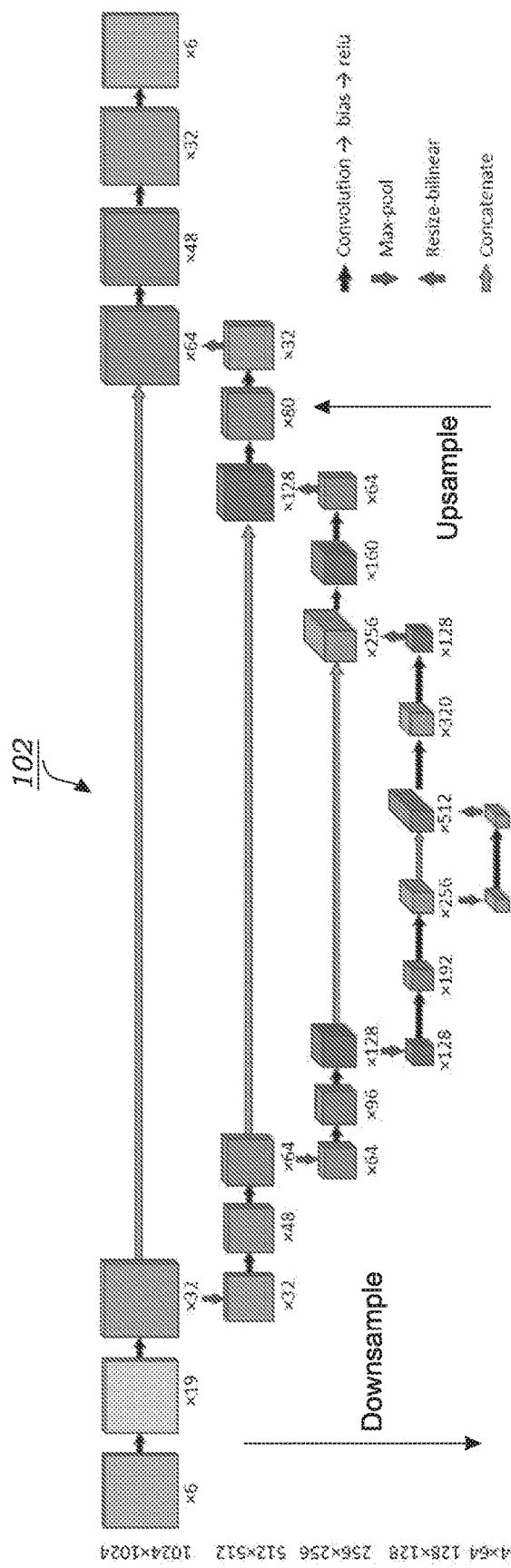
FIG. 9A illustrates the architecture of the convolutional neural network (CNN) used for holographic image reconstruction. The input matrix is 1024×1024 pixels each, for RGB intensity (×3) and RGB phase channels (×3), i.e., altogether forming 6 channels. The network output is the phase-recovered and twin-image eliminated RGB intensity and RGB phase of the flowing object. These can be merged to create the final phase-contrast image of the object.
Figure 9B:
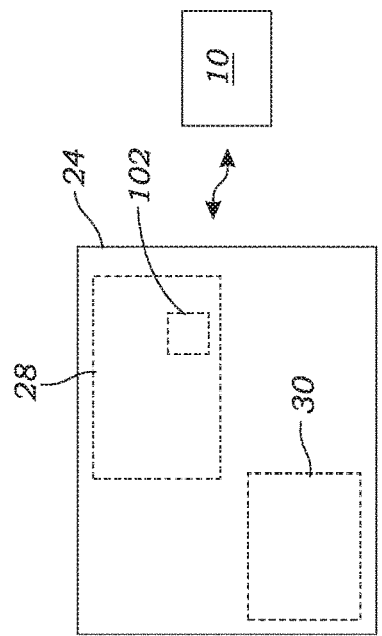
FIG. 9B schematically illustrates a computing device that interfaces with the imaging flow cytometer device. The computing device includes image processing software and control software for controlling various aspects of the imaging flow cytometer device.

As illustrated in FIGS. 1 and 9B, the system 2 further includes a computing device 24 that is operatively connected to the imaging flow cytometer device 10. The computing device 24, in one embodiment, is used to control various operational aspects of the flow cytometer device 10 using control software 30 and/or image processing software 28.

This includes controlling the rate at which the fluid containing the objects 12 is pumped through the imaging flow cytometer device 10, imaging parameters such as the intensity of the various colored light sources are that are described herein, and camera settings (e.g., frame rate, exposure time for the LEDs, gain, color ratios, and the like).

Figure 5:
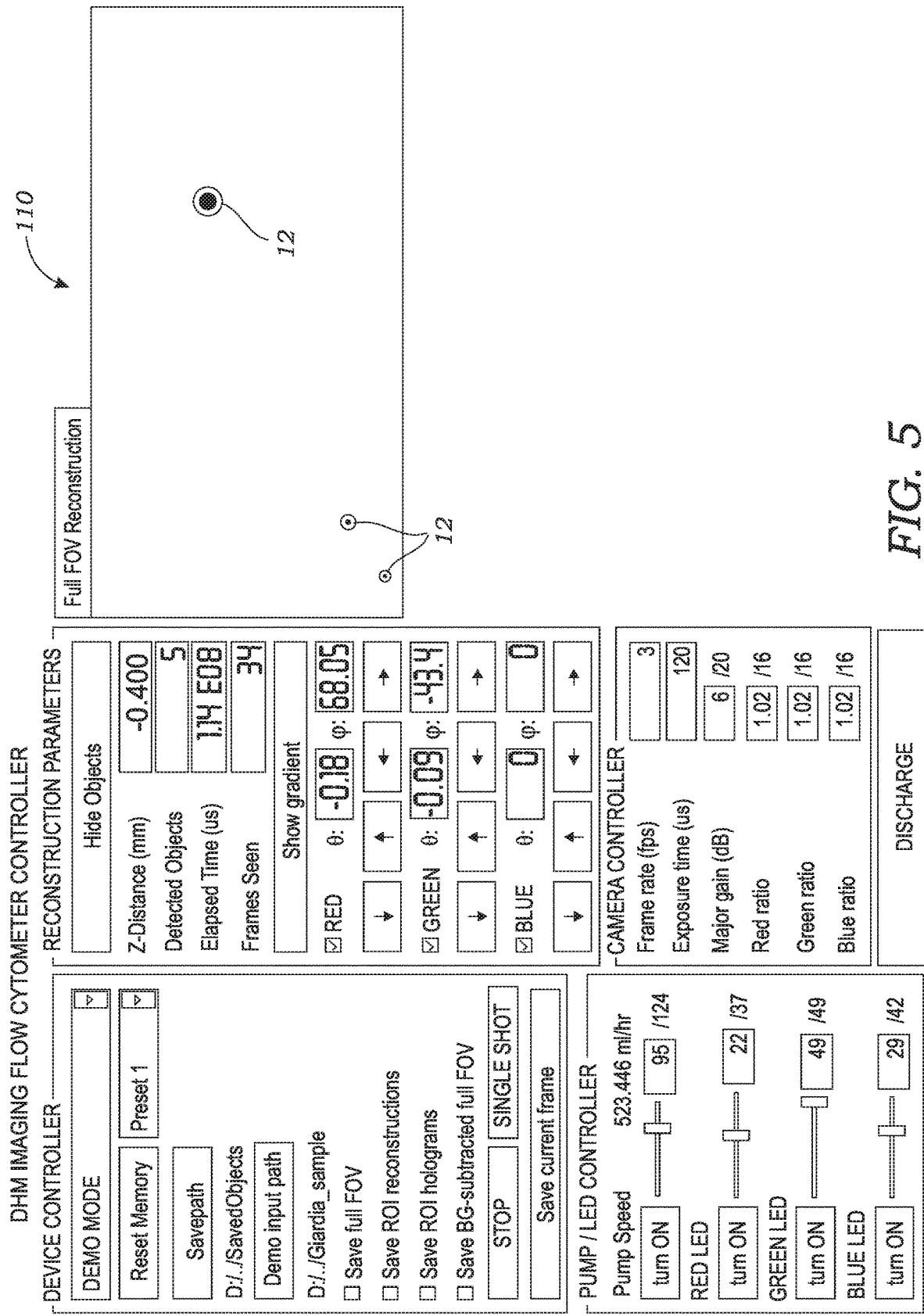
FIG. 5 illustrates one example of the graphical user interface (GUI) that is used on the computing device (e.g., laptop computer) that is used in connection with the imaging flow cytometer device. The image shows the full field-of-view (FOV).
Figure 6:
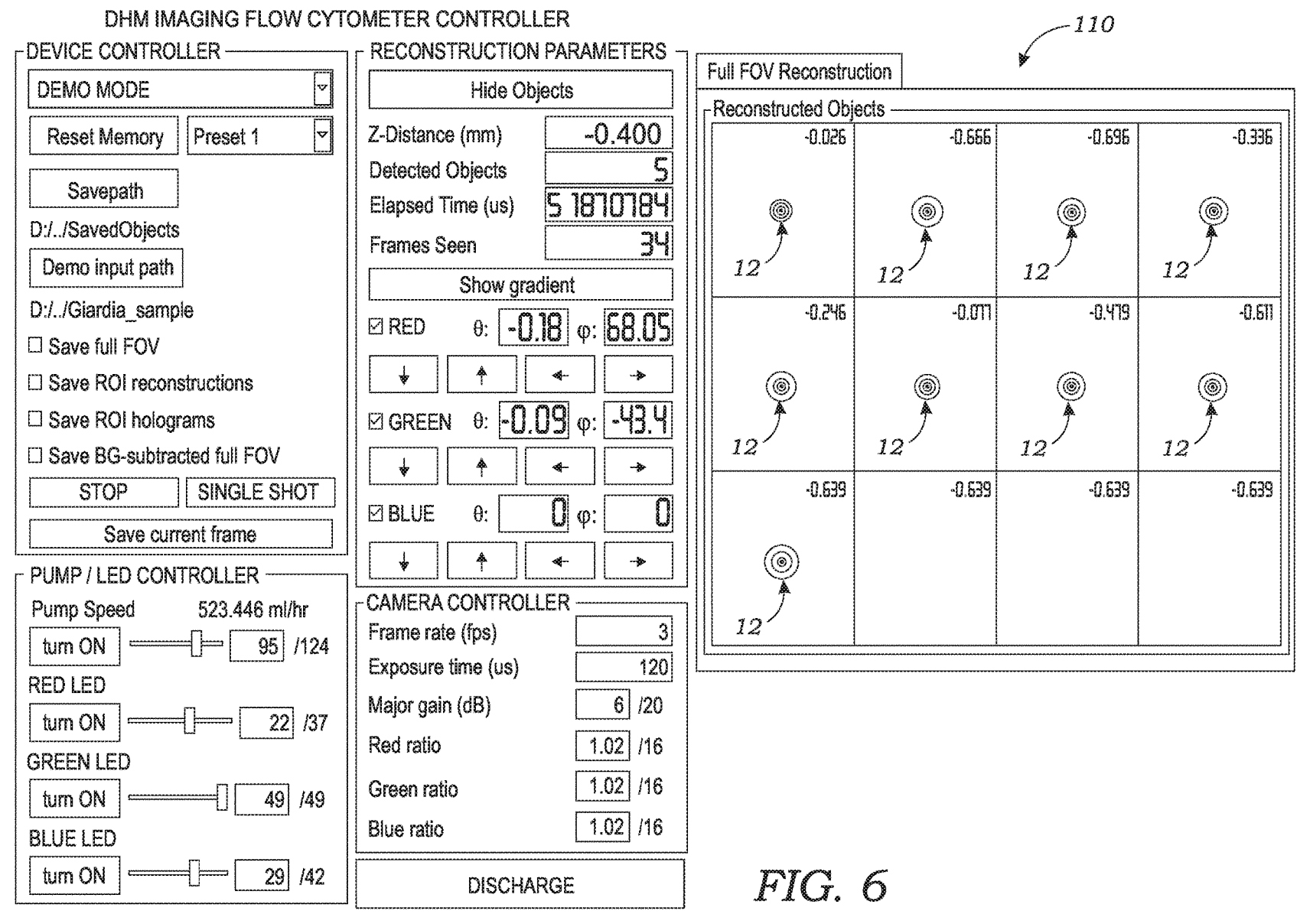

The control software 30 and/or image processing software 28 of the computing device 24 may also be used to view, control, or modify the reconstruction parameters that are used to reconstruct phase and amplitude images as described herein. The control software 30 and/or image processing software 28 may also be used to calibrate the parameters needed for reconstruction of higher-resolution images of the objects. This includes angle compensation ($\theta$, $\Psi$) for the red, green, and blue LEDs. The control software 30 and/or image processing software 28 of the computing device 24 may also be used to view and save various images (including hologram images, reconstructed images, and phase-recovered images). For example, in one particular embodiment, the phase recovered intensity image and phase recovered phase image are combined or merged to generate a phase recovered phase-contrast image of the object(s) 12. These may be displayed on a display 26 or the like associated with the computing device 24. FIGS. 5 and 6 illustrate an exemplary graphical user interface (GUI) 110 that be used to view data and images as well as control various operational aspects of the imaging flow cytometer device 10.

The computing device 24, in one embodiment, contains image processing software 28 that is used to perform imaging and other operations as described more fully herein. This includes, for example, image pre-processing operations such as background subtraction, image resample, object segmentation, object focusing operations. The image processing software 28 also performs the high-resolution color reconstruction in which hologram images are reconstructed into intensity and/or phase images. The image processing software 28 may also execute the trained neural network (e.g., deep neural network or DNN) used to generate phase recovered intensity and/or phase images (or phase recovered phase-contrast images that merge these two). The trained neural network may also be used to identify or classify the type of object(s) 12 that are imaged.

The image processing software 28 is also used for the acquisition and storage of the many image files that are collected during the operation of the imaging flow cytometer device 10. In some modes, real time data and images may be generated by the image processing software 28. In other modes, the image processing software 28 may be used to analyze images that have previously been captured and then transferred to the computing device or to storage media accessible by the computing device 24. The transfer of image files may occur via wire or a wireless transmission. In some embodiments as noted herein, the image processing software 28 is able to automatically identify or classify the object 12. For example, in the context of using the imaging flow cytometer device 10 to evaluate water bodies, the image processing software 28 may identify the type of plankton or other microorganism. Type may refer to particular species of microorganisms or it may refer to a particular phenotype.

The image processing software 28 may be integrated into the control software 30 that is used to control various operational aspects of the imaging flow cytometer device 10. In some embodiments, however, the control aspects of the imaging flow cytometer device 10 may be run by control software 30 that is separate from the image processing software 28. In this regard, the control software 30 may reside on a first computing device 10 while the image processing software 28 may reside on a second computing device 24. For example, a local computing device 24 may be used to control the imaging flow cytometer device 10 with the control software 30 while a remotely located computing device 10 (e.g., server, cloud computer, etc.) may execute the image processing software 28. Of course, as illustrated in FIG. 1, a single computing device 24 may operate the image processing software 28 and the control software 30.

The computing device(s) 24 that may be used with the flow cytometry imaging system 2 may include any number of computing devices such as personal computers (PCs), laptops, tablet computers, mobile phones (e.g., Smartphones), servers, and the like. As noted herein, the image processing software 28 is preferably executed on a computing device 24 that has one or more graphics processing unit (GPU) which increases the speed at which images or other output are generated by the image processing software 28. The computing device(s) 24 may interface with the imaging flow cytometer device 10 via a wired (e.g., USB or the like) and/or wireless connection (Wi-Fi, Bluetooth, or the like). The imaging flow cytometer device 10 may be powered by power supply that can be connected to an AC outlet (and converted by power supply to 5V DC). Alternatively, the imaging flow cytometer device 10 may be powered by one or more batteries (e.g., 5V battery pack) that may be internal or external to the housing or enclosure 18.

Still referring to FIG. 1, the imaging flow cytometer device 10 is used in connection with source of fluid that contains object(s) 12 therein. The source of fluid may be contained in receptacle 32 like a test tube, cuvette, vial, or the like. Two such receptacles 32 are provided as illustrated in FIG. 1. Each receptable 32 is connected via tubing 34 to an inlet 40 and outlet 42 (best seen in FIG. 2), respectively of the microfluidic device 16 that contains the microfluidic channel 14 as described herein. A first receptacle 32 is used to draw fluid into the imaging flow cytometer device 10 while a second receptacle 32 is used to receive fluid that has passed through the imaging flow cytometer device 10. Thus, one receptacle 32 is used for fluid input while the other receptacle 32 is used for fluid output. The source of fluid 32 that is contained in the receptacle 32 that is run through the imaging flow cytometer device 10 is one embodiment, an aqueous or water-based fluid. The water-based fluid may contain a sample of water obtained at a natural or artificial water body. Examples includes oceans, rivers, lakes, streams, ponds, potable water sources, and the like.

Figure 2:
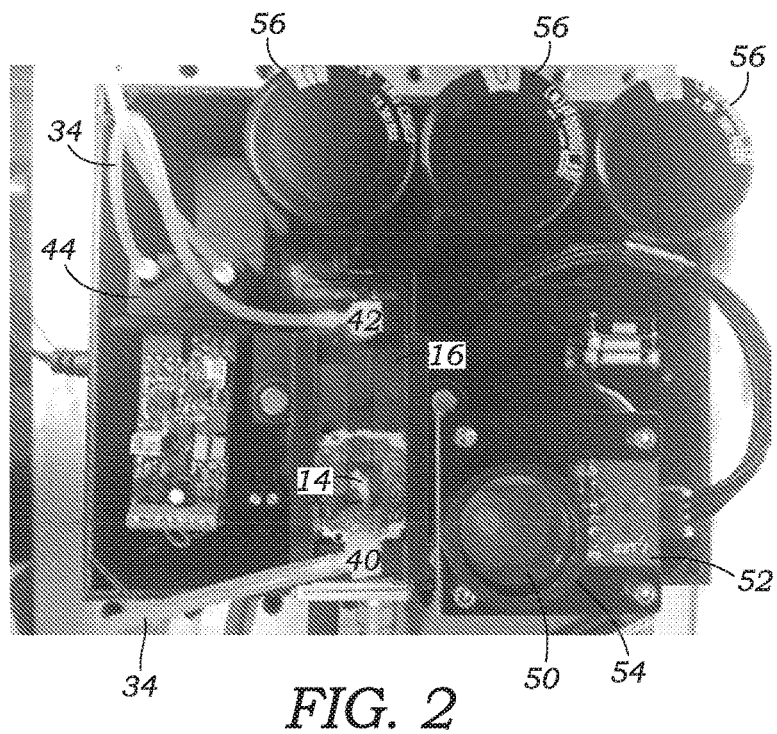
FIG. 2 illustrates a photograph taken of the imaging flow cytometer device with the enclosure or housing opened.

Referring to FIGS. 1 and 2, the imaging flow cytometer device 10 includes a microfluidic device 16 that has a microfluidic channel 14 formed therein that communicates with an inlet 40 and outlet 42. The microfluidic device 16 may be formed as a laminate or as a monolithic structure and is held within a holder 39 within the housing or enclosure 18. The microfluidic device 16 may take the form of a chip or flow cell, for example. The microfluidic device 16 may be inserted and removed from this holder 39 as needed (e.g., the microfluidic device 16 may be a disposable component that is replaced after each use). The microfluidic device 26 is formed from an optically transparent material (e.g., optically transparent polymer or glass) so that light from the light source is able to pass through the microfluidic channel 14 such that holographic images of object(s) 12 contained in the fluid can be captured by an image sensor as explained herein. The dimensions of the microfluidic channel 14 may vary from tens or hundreds of micrometers up to more than 1 mm. The size of the microfluidic channel 14 should be large enough such that the microfluidic channel 14 does not clog in response to fluid flow. The tested microfluidic channel 14 described herein had a height of 800 μm and a width of around 5 mm). By increasing the cross-sectional dimensions (e.g., height or width) higher throughput rates can be achieved.

A pump 44 is disposed in the housing or enclosure 18 and is used to pump the fluid containing the object(s) 12 from the receptacle 32 and into the microfluidic channel 14 of the microfluidic device 16. Fluid leaves the receptacle 32 and is pumped via the pump 44 into the inlet 40 where the fluid continues down the microfluidic channel 14 and then exits via outlet 42. The fluid leaving the microfluidic device 16 is emptied into the receiving receptacle 32 via tubing 34. The pump 44 may include a peristaltic pump (e.g., Instech p625) such as described herein. Other types of pumps 44 include microfluidic pumps or any other pump that can pump fluid through the microfluidic channel 14. The flow rate of the pump 44 may be varied using the control software 30. In some embodiments, the presence of the pump 44 in the imaging flow cytometer device 10 is optional. For example, the pump 44 may be external to the imaging flow cytometer device 10. In another embodiment, the imaging flow cytometer device 10 may be placed in-line with another system or process and that pumped flow may be used to push or pull fluid through the microfluidic channel 14.

An image sensor 46 is disposed adjacent to the microfluidic device 16 and microfluidic channel 14 such that the active area of the image sensor 46 encompasses the area of the microfluidic channel 14. The active area of the image sensor 46 may be centered on the center of the microfluidic channel 14 as described herein. A small air gap of several microns or the like may be present the bottom surface of the microfluidic channel the active area of the image sensor 46, although the active area could be in contact with the surface of the microfluidic channel 14 in other embodiments. In one embodiment, when a multi-colored light source is used, the image sensor 46 that is used is a color image sensor 46. An example of such a color image sensor includes a camera 47 that has a CMOS color image sensor 46 (e.g., Basler aca4600-10uc (Basler AG, Germany) with a pixel size of 1.4 μm. The color image sensor 46 may be powered via a cable (e.g., USB cable) that also is used to transfer images (i.e., image frames) that are captured by the color image sensor 46. In some other embodiments, the imaging flow cytometer device 10 may used a monochrome image sensor 46. In such an embodiment, a multi-color light source is not needed. For example, a monochrome image sensor 46 may be used when lower-level resolution is needed such as object counting and the like.

A light source 50 is disposed in the housing or enclosure 18 and is used to provide the illumination that is used to illuminate the object(s) 12 contained in the fluid that flows through the microfluidic channel 14. In one embodiment, the light source 50 is a multi-colored light source that emits light at a plurality of discrete wavelength ranges or bands. For example, a multi-colored LED may be used to emit red, green, and blue light. An example includes a surface mountable RGBW LED that has individually addressable red, blue, and green LED dies that are used to create the multi-color light that are driven simultaneously to illuminate the microfluidic channel 14 containing the flowing fluid. An example of such a multi-colored light source 50 is LZ4-04MDPB emitter made by LED Engin (Osram). Triple-output LED driver controller circuitry 52 (LT3797, Linear technologies Driver) is provided to drive the light source 50.

Referring to FIGS. 1 and 4A, in one embodiment, a plurality of filters 54 are provided to adjust the coherence of the light that illuminates the microfluidic channel 14. FIG. 1 illustrates two such filters 54 that are triple bandpass optical filters (Edmund Optics #87-246, Chroma Inc. 69015m) to increase the temporal coherence of the illumination. The filters are spaced apart with a spacer 55 and held in a holder 57 and retained by a cap 59 (seen in FIG. 4A). It should be understood, however, that in other embodiments only a single filter 54 may be needed. In still other embodiments, where the coherence of the light source 50 is sufficiently narrow, a filter 54 may not even be needed.

During operation of the imaging flow cytometer device 10, the different LEDs of the multi-colored light source 50 are simultaneously illuminated in a pulse. The image sensor 45 is operated in global reset release mode and the pulse width is adjusted to not allow an object 12 traveling at the maximum speed inside the microfluidic channel 14 to shift by more than the width of a single sensor pixel. For a flowrate of 100 mL/h, this corresponds to a pulse length of 120 μs.

To pulse the different LEDs, high-current pulses are stored in three 0.1-F-capacitors 56, which are charged using a capacitor charger controller 58 (LT3750, Linear Technologies) to 12 V. The capacitor charge is initiated by the image sensor flash window trigger signal, which is active during the frame capture, and its length can be controlled by the camera/image sensor 46 software driver. The charger controller 58 acquires an "on" state and keeps charging the capacitors until the pre-set voltage level of 12 V is reached. During the short illumination pulses, the voltage on the capacitors decreases only slightly, and they are immediately recharged as each frame capture resets the charge cycle, thereby allowing continuous operation.

The LEDs are synchronized and their constant-current operation is ensured by the drive circuitry 52. The controller 58 uses the same flash window signal from the image sensor 46 to turn on the LEDs of the light source 50 for the exposure duration set by the software. The current of each LED is kept constant for the subsequent pulses by the circuit, thus, maintaining the same illuminating intensity for each holographic frame.

In another alternative embodiment, the light source 50 is operated in a continuous wave operation that does not generate pulses of light. For example, the multi-color LEDs of the light source 50 may be emit light simultaneously over a continuous period of time (e.g., while sample analysis is being performed) while the image sensor 46 is operated in a "pulsed" mode to capture a plurality of image frames. The image sensor 46 may be operated with, for example, very fast shutter/image capture speeds using various options well known to modern camera systems. In this regard, similar images are produced of the moving objects 12 but instead of pulsing the light source 50 the image sensor 46 is operated in a pulse mode. Of course, use of the continuous wave light source 50 obviates the need for the capacitors 56 and associated charge controller 58.

Figure 4B:
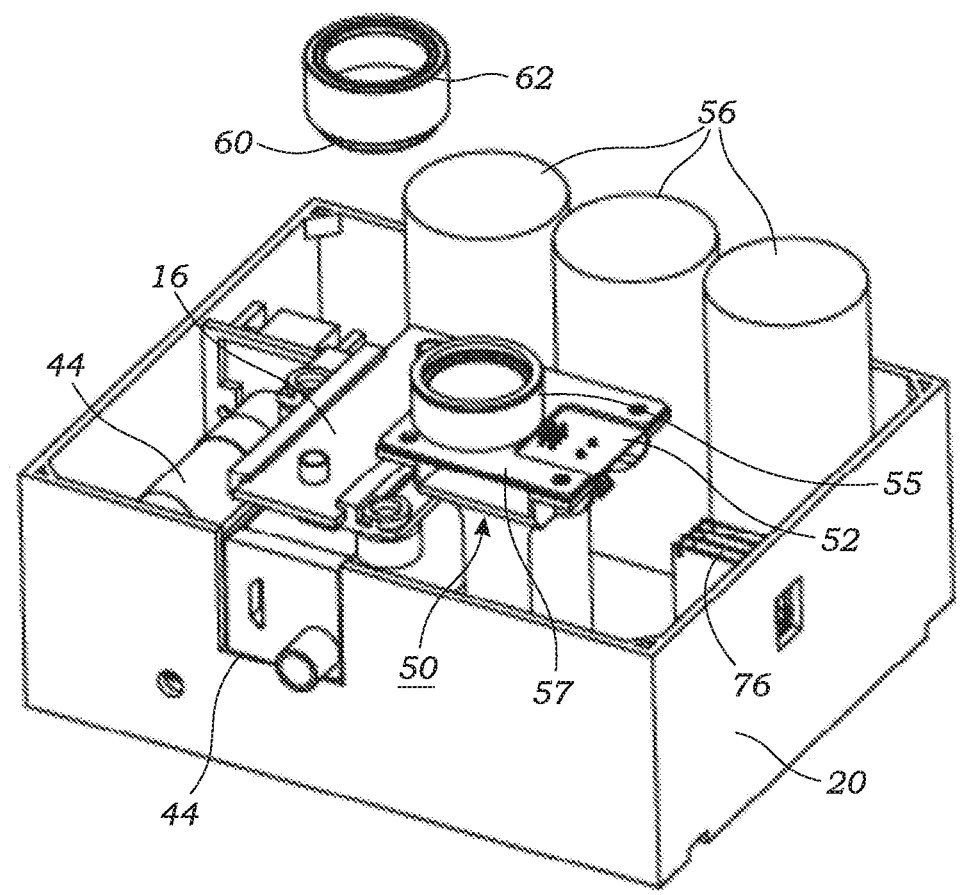
FIG. 4B illustrates a perspective view of the assembled imaging flow cytometer device of FIG. 4A with the top or lid removed for clarity (the mirror and mirror mount are visible).

Referring to FIGS. 1, 4A, 4B, the housing or enclosure 18 includes a mirror 60 that in one embodiment is a convex mirror 60 that is mounted in the lid or top portion 22 with a mirror mount 62. The mirror 60 reflects light from the light source 50 before reaching the microfluidic channel 14 so as to increase the spatial coherence while allowing a compact and light-weight optical setup. In this regard, a folded optical path is formed whereby light that is emitted by the light source 50 is reflected onto the microfluidic channel 14 whereby holograms of object(s) 12 within the flowing fluid are cast upon and captured by the image sensor 46. In an alternative configuration, the optical path between the light source 50 and the microfluidic channel 14 is not folded, however, this will move the light source 50 further away and increase the overall size of the device 10. While a single reflection is used as part of the folded optical path it should be appreciated that additional reflections (i.e., folded light paths) may be used beyond the one illustrated.

As best seen in FIG. 4A, a frame or support 64 is provided and secured within the bottom portion 20 of the housing 18 that holds the various components. This includes, for example, a mount 66 for the camera 47 as well as a mount or holder 68 for the LED drive circuitry 52 and light source 50 (e.g., LED chip). A separate mount 70 is provided for the pump 44. A mount 72 is also provided for the microfluidic device holder 39. The frame 64 also includes a mount 74 for a microcontroller 76 which is used as an interface for i2c communications.

EXPERIMENTAL

Figure 10:
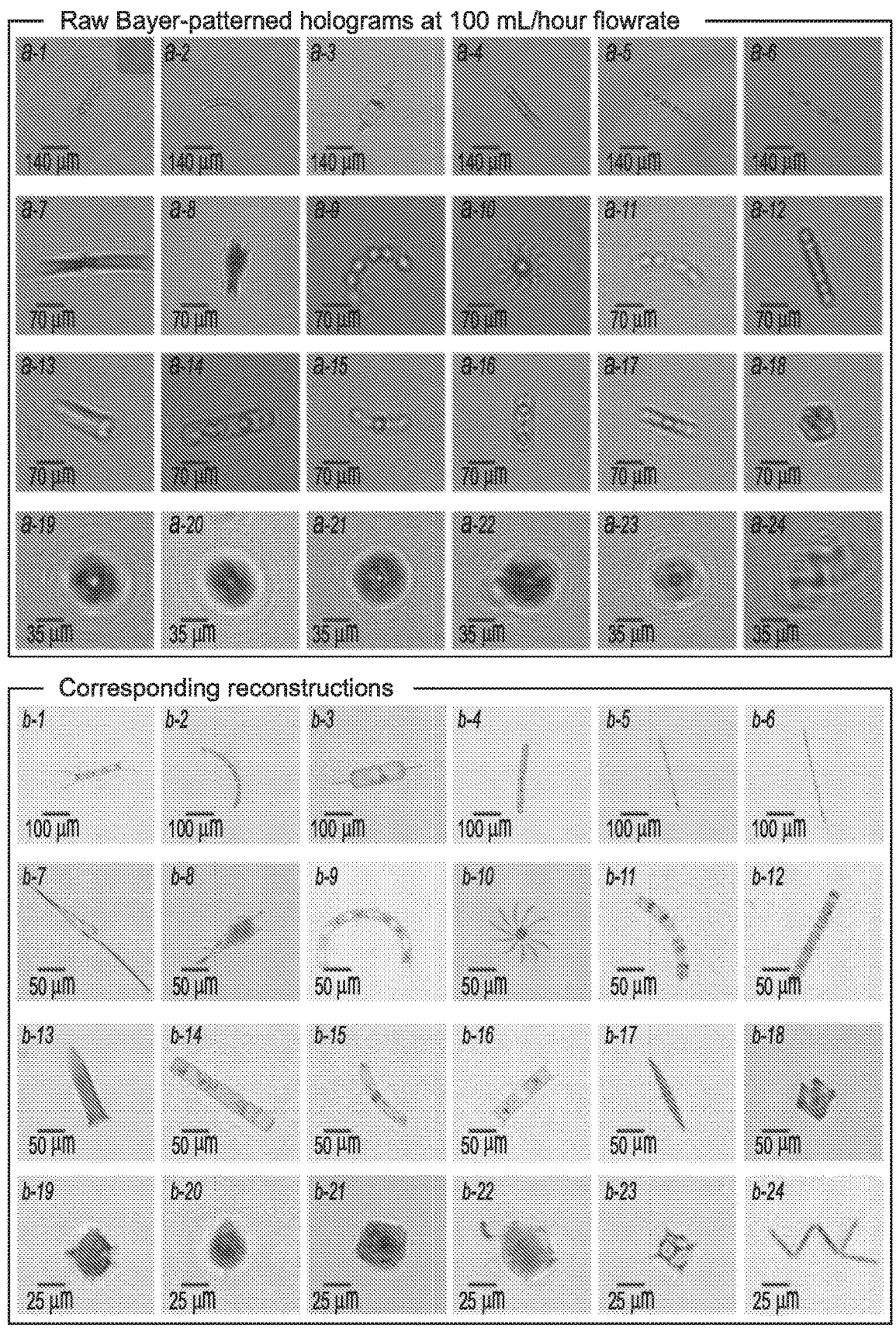
FIG. 10 illustrates images of various ocean plankton detected by the imaging flow cytometer at the Los Angeles coastline, represented by their (a-1 through 1-24) raw holograms, and (b-1 through b-24) phase-contrast reconstructions, following phase recovery. Organisms are identified as: (1) *Chaetoceros lorenzianus*, (2) *Chaetoceros debilis*, (3) *Ditylum brightwelli*, (4) *Lauderia*, (5) *Leptocylindrus*, (6) *Pseudo-nitzschia*, (7) *Ceratium fusus*, (8) *Ceratium furca*, (9) *Eucampia cornuta*, (10) *Bacteriastrum*, (11) *Hemiaulus*, (12) *Skeletonoma*, (13) *Ciliate*, (14) *Cerataulina*, (15) *Guinardia striata*, (16) *Lithodesmium*, (17) *Pleurosigma*, (18) *Protoperidinium claudicans*, (19) *Protoperidinium steinii*, (20) *Prorocentrum micans*, (21) *Lingulodinium polyedrum*, (22) *Dinophysis*, (23) *Dictyocha fibula* (silica skeleton), and (24) *Thalassionema*. The dashed rectangle in the panel (a-1) represents the segmented and 45° rotated area corresponding to the reconstructed images.
Figure 11:
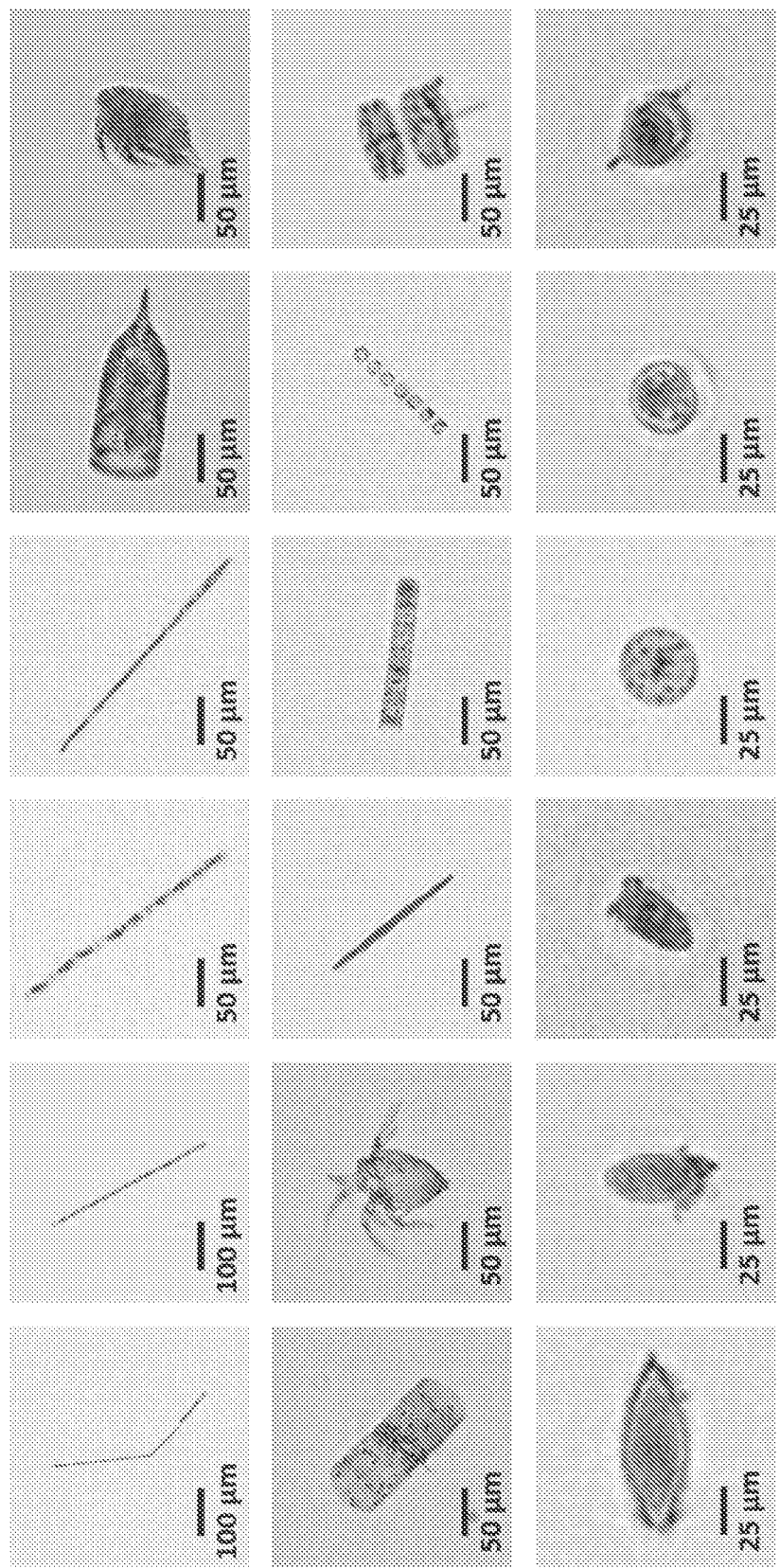
FIG. 11 illustrates phase-contrast color images depicting the plankton found near the Los Angeles coastline and imaged by the flow cytometer at a flowrate of 100 mL/h.
Figure 12:
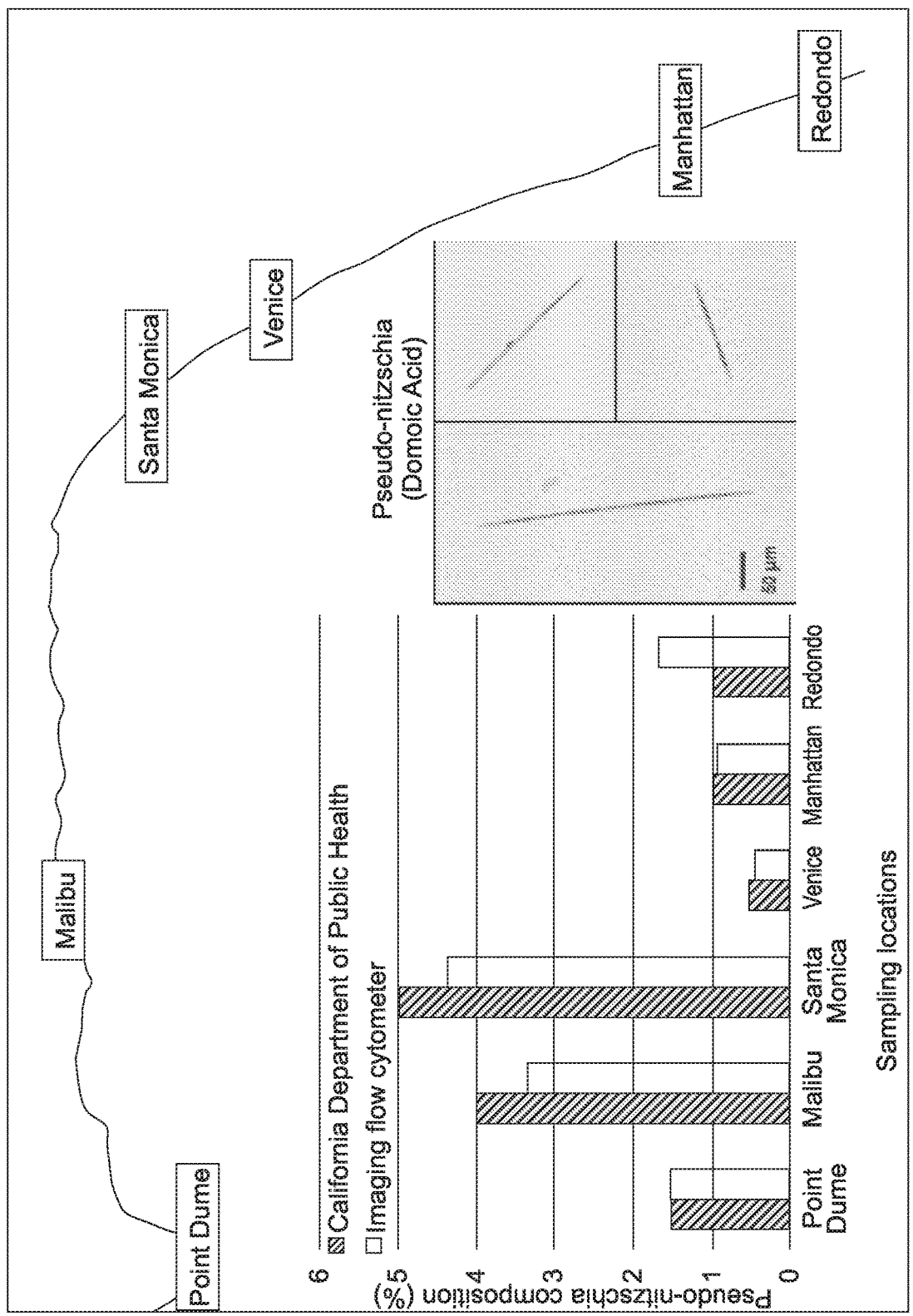
FIG. 12 illustrates a map of the Los Angeles area coastline along with a graph showing the prevalence of *Pseudo-*

The imaging flow cytometer device 10 was tested with water samples obtained from the ocean along the Los Angeles coastline. The samples were imaged at a flow rate of 100 mL/h and the raw full FOV image information was saved on computing device 24 in the form of a laptop that was also used to control operation of the imaging flow cytometer device 10. Plankton holograms were segmented automatically as described herein in more detail (e.g., FIGS. 7, 8 and related descriptions) and reconstructed by the computing device 24 using a deep convolutional network, and the phase-contrast color images of plankton were calculated and saved to the local laptop computing device 24 that also controlled the imaging flow cytometer through a custom-designed GUI 110 as illustrated in FIGS. 5 and 6. FIG. 10 highlights the performance of the automated deep learning-enabled reconstruction process employed by the image processing software executed by the computing device 24 and the image quality achieved by the imaging flow cytometer device 10, showcasing several plankton species with both their initial segmented raw images (holograms) and the final-phase contrast images (which are in color in one preferred embodiment). Most of these plankton types were detected by the imaging flow cytometer device 10 based on the reconstructed images, as detailed in FIG. 10 images. An additional selection of unidentified plankton imaged in the same ocean samples is also shown in FIG. 11. Some part of the water sample for each measurement was also sent to CDPH for comparative microscopic analysis by their experts, and the qualitative composition of different species found in each water sample was in good agreement with the measurements obtained with the imaging flow cytometer device 10. Furthermore, to perform a quantitative comparison against the routine analysis performed by CDPH, the potentially toxic *Pseudo-Nitzschia* algae was selected and its relative abundance was evaluated at six different measurement locations (i.e., public beaches) along the Los Angeles coastline. The imaging flow cytometer results, summarized in FIG. 12, also show good agreement with the analysis performed by the CDPH.

The field portability of the imaging flow cytometer device 10 was demonstrated by on-site operation of the imaging flow cytometer device 10 at the Redondo Beach pier where experiments were performed over a duration of 8 h. The imaging flow cytometer device 10 itself was powered by a 5 V battery pack and could run for several hours. A 500-Wh 19-V external battery pack was used to power the laptop computing device 24 for the duration of the field experiments (from 6:30 AM to 2:30 PM). In these field experiments, the time evolution of the total plankton concentration was measured in the ocean during the morning hours and found that the amount of microplankton in the top 1.5 m of the water increases during the day possibly owing to vertical migration (see FIG. 13). The number of *Pseudo-Nitzschia* found in these samples was manually counted as well and observed a peak in the morning (at ~8:30 AM) and a steady decline after that (FIG. 13); in general these trends are rather complicated to predict since they are influenced by various factors, such as the composition of the local microbiome, tide and upwelling/downwelling patterns. These results demonstrate the capability of the imaging flow cytometer device 10 to periodically measure and track the plankton composition and concentration of water samples on site for several hours without the need to be connected to a power grid.

The throughput of any imaging flow cytometer is determined by several factors, but most importantly it is governed by the required image quality. The imaging flow cytometer device 10 was designed to achieve the highest resolution that is allowed by the pixel size of the image sensor 46, which resulted in a tight photon budget owing to the loss of illumination intensity for achieving sufficient spatial and temporal coherence over the sample volume, and the requirement for pulsed illumination for eliminating motion blur. Because of the fast flow speed of the objects 12 within the microfluidic channel 14, pixel super-resolution approaches could not be used to improve the resolution of the reconstructed images to sub-pixel level. Experiments were conducted at 100 mL/h; however, at the cost of some motion blur this throughput could be quadrupled without any modification to the device 10. It could be increased even more by using a microfluidic channel 14 with greater height (e.g., >1 mm). To demonstrate this, an ocean sample was imaged with increased throughputs of up to 480 mL/h (see FIGS. 14A-14F). The obtained reconstructions show that the imaged alga (*Ceratium Furca*) still remains easily recognizable despite the increased flow speed.

In addition to the physical volumetric throughput, the processing speed of the computing device 24 (e.g., laptop) can also be a limiting factor, affecting mainly the maximum density of the sample that can be processed in real time. The imaging flow cytometer device 10 design achieves real-time operation, i.e., the computing device 24 processes the information faster than the image sensor 46 provides it to avoid overflowing the memory. Currently, the imaging flow cytometer device 10 can be run in three modes depending on the sample density. In a first mode, the imaging flow cytometer device 10 can acquire and save the full FOV holograms and perform all the reconstruction and phase recovery steps after the measurement, which is a necessary approach for high-concentration samples (e.g., >2,000-3,000 objects/mL). Even denser samples can also be analyzed by the imaging flow cytometer device 10 device by e.g., diluting them accordingly or by lowering the throughput. In a second mode, the image processing software of the computing device 24 can reconstruct the holograms but not perform phase recovery of the detected objects 12 during the measurement. At present, the image segmentation and reconstruction procedure takes~320 ms for each full FOV frame, in which seven (7) objects can be reconstructed per image with parallel computing on a GTX 1080 GPU. The major computational operations are: (1) segmentation of the full FOV hologram for object detection (~70 ms), (2) holographic autofocusing and reconstruction (~12 ms/object), and (3) transfer of the final amplitude and phase images (8 bit, 1024×1024 pixels×3 color channels) from the device (i.e., GPU) to the host (i.e., central processing unit) and saving them on an internal solid-state drive (~10-20 ms per object). Consequently, in case of reconstructing but not phase recovering the objects 12, the imaging flow cytometer device 10 can image, in real-time, samples with ~700 objects/mL at a flowrate of 100 mL/h.

In the third mode of operation, the imaging flow cytometer device 10 involves performing both the image reconstruction and phase recovery steps for all the flowing objects 12 during the measurement. The deep learning-based phase recovery step is currently the most intensive part of the image processing algorithm with a runtime of ~250 ms/object. Thus, if real-time phase recovery is necessary in this third mode of operation, it restricts the sample density to ~100 objects/mL at a flowrate of 100 mL/h. Since the performance of GPUs increases on average 1.5×per year, these computational performance restrictions will be partially overcome over time as GPU performance improves with time. Furthermore, it is possible to simultaneously focus all the objects in a hologram using a convolutional neural network that extends the depth-of-field of holographic reconstruction by >25-fold compared to conventional approaches. This would allow combining the phase recovery, auto-focusing and image reconstruction steps into a single neural network, making the computation time for the full FOV independent of the density of the particles, enabling real-time imaging of highly dense fluidic samples. Indeed, this approach was tested to reconstruct objects 12 in the 800 µm (height) microfluidic channel 14 and found that it gives good results regardless of the height of the objects 12 inside the microfluidic channel 14 (see FIG. 15).

Although the tested imaging flow cytometer device 10 is a field-portable, this particular embodiment was not fully waterproof and operated above the water surface. This prototype can operate up to 100 meters away from the controlling computing device 24 (e.g., laptop) by simply changing the USB3 camera connection to GigE, and constructing a long-range microcontroller communication setup similar to an OpenROV submersible platform. Owing to its low hardware complexity in comparison with other imaging flow cytometer technologies, the component cost of the system 2 is very low (<$2,500), and with large volume manufacturing, it could be built for less than $760 (see Table 1 below). This remarkable cost-effectiveness opens up various exciting opportunities for environmental microbiology research and could allow the creation of a network of computational imaging cytometers at an affordable price point for large-scale and continuous monitoring of ocean plankton composition and ocean microbiome (or other water bodies) in general.

TABLE 1

| Component | Single Unit (USD) | High Volume (USD) |
|---|---|---|
| Pump | $700 | ~$420 |
| Image Sensor | $676 | ~$115 |
| Illumination Circuit | ~$300 | ~$110 |
| Optical Filters | $400 + $375 | <$100 |
| Flow Channel | ~$15 | <$10 |
| Total | ~$2466 | <$755 |

Methods
Optical System

The imaging flow cytometer device 10 uses a color image sensor 46 with a pixel size of 1.4 µm (Basler aca4600-10uc). The housing of the camera 47 is removed, and the circuit is rearranged to allow the microfluidic device 16 to be directly placed in contact with the protective cover glass of the image sensor 46 (see FIGS. 1 and 3). There may be a small air gap (several micrometer) located between the bottom of the microfluidic device 16 and the image sensor 46. The illumination of the imaging flow cytometer device 10 is provided by using the red, green, and blue emitters from an LED light source 50 (Ledengin LZ4-04MDPB). The spatial and temporal coherence of the emitted light from the LED-based light source 50 is increased to achieve the maximum resolution allowed by the sensor pixel size. The spatial coherence is adjusted by using a convex mirror 60 (Edmund optics #64-061) to increase the light path. The LED light is also spectrally filtered by two triple bandpass optical filters 54 (Edmund Optics #87-246, Chroma Inc. 69015m) to increase the temporal coherence of the illumination. The placement of the optical components is designed to tune the bandpass of the spectral filter angle to better match the emission maximum of the LEDs. Increasing the spatial and temporal coherence of the LEDs also decreases the intensity reaching the image sensor 46. In addition, the short exposure time required to avoid the motion blur when imaging objects 12 in a fast flow makes it necessary for our configuration to utilize a linear sensor gain of 2. The additional noise generated from the gain is sufficiently low to not interfere with the image reconstruction process.

Microfluidic Channel and Flow Design

A microfluidic channel 14 (Ibidi µ-Slide I) with an internal height of 0.8 mm is placed on the top of the image sensor 46, secured using a 3D-printed holder 39, and connected to a peristaltic pump 44 (Instech p625). The size of the active area of the image sensor 46 is slightly smaller than the width of the microfluidic channel 14 (4.6 mm vs. 5 mm), and the microfluidic channel 14 is so positioned that the image sensor 46 measures the center of the liquid flow. The flow profile inside the microfluidic channel 14 was calculated (see FIG. 14F) by solving the Navier-Stokes equation for non-compressible liquids assuming a non-slip boundary condition. The results show that the image sensor measures~98% of the total volume passing through the microfluidic channel 14. The flow profile is a two-dimensional paraboloid, with the maximum flow speed located at the center of the microfluidic channel 14, measuring approximately 1.66 times higher than the mean velocity of the liquid (see FIG. 14F). To acquire sharp, in-focus images of the objects 12 in the continuously flowing liquid, the image sensor 46 was operated in the global reset release mode and illuminated the sample by flash pulses, where the length of an illuminating pulse is adjusted to not allow an object 12 traveling at the maximum speed inside the microfluidic channel 14 to shift by more than the width of a single sensor pixel. For a flowrate of 100 mL/h, this corresponds to a pulse length of 120 µs.

Pulsed Illumination, Power, and Control Circuit

Because shortening the illumination time also constrains the available photon budget, the brightness of the LED light source 50 was maximized by operating them at currents ranging from of 2.2-5 A depending on the LED color. The currents are set for each LED emitter to create similar brightness levels at the image sensor 46, ensuring that the sample is adequately lit at each color, a requirement for obtaining color images. The green LED spectrum is inherently wider than the red and blue counterparts, and so, the spectral filters 54 will reduce its intensity the most. Therefore, the green LED was operated at the experimentally determined maximum possible current of 5 A. The red and blue LEDs require a current of ~2.2 A for matching the intensity of the green LED on the image sensor 46 for correcting the white balance. Control circuitry was utilized to control the components of the imaging flow cytometer device 10. The circuit is powered by either a 5-V-wall-mount power supply or a cellphone charger battery pack. The control circuitry fulfills four major roles of providing power to the peristaltic pump 44, charging the capacitors 56 for providing power to the LED-based light source 50, synchronizing the LEDs to the image sensor 46 and creating stable, short, high current pulses, and finally, providing an interface for remote control via the computing device 24 using Inter-Integrated-Circuit (i2c) interface for setting various parameters. The peristaltic pump 44 is powered by a high-efficiency step-up DC-DC converter at 16 V (TPS61086, Texas instruments), and its speed is controlled by a potentiometer via i2c components (TPL0401B, Texas Instruments). The charge for the high-current pulses is stored in three 0.1-F-capacitors 56, which are charged using a capacitor charger controller 58 (LT3750, Linear Technologies) to 12 V. The capacitor charge is initiated by the image sensor flash window trigger signal, which is active during the frame capture, and its length can be controlled by the camera software driver. The charger controller 58 acquires an "on" state and keeps charging the capacitors 56 until the pre-set voltage level of 12 V is reached. During the short illumination pulses, the voltage on the capacitors 56 decreases only slightly, and they are immediately recharged as each frame capture resets the charge cycle, thereby allowing continuous operation. The LEDs are synchronized and their constant-current operation is ensured by a triple-output LED driver controller 52 (LT3797, Linear technologies). The controller 52 uses the same flash window signal from the image sensor 46 to turn on the LEDs of light source 50 for the exposure duration set by the software. The current of each LED is controlled between 0-12.5 A using digital i2c potentiometers (TPL0401B, Texas Instruments), and it is kept constant for the subsequent pulses by the circuit 52, thus, maintaining the same illuminating intensity for each holographic frame. During startup, it takes~3-4 frames for the circuit 52 to stabilize at a constant light level. To avoid having multiple devices with the same address on the i2c line, an address translator was used (LTC4317, Linear Technologies) to interface with the potentiometers controlling the red and blue LEDs. To control the circuit, the computing device 24 (e.g., laptop) communicates with an Arduino microcontroller 76 (TinyDuino from Tinycircuits), which is used as an interface for i2c communications only.

Object Detection and Deep Learning-Based Hologram Reconstruction

Figure 7:
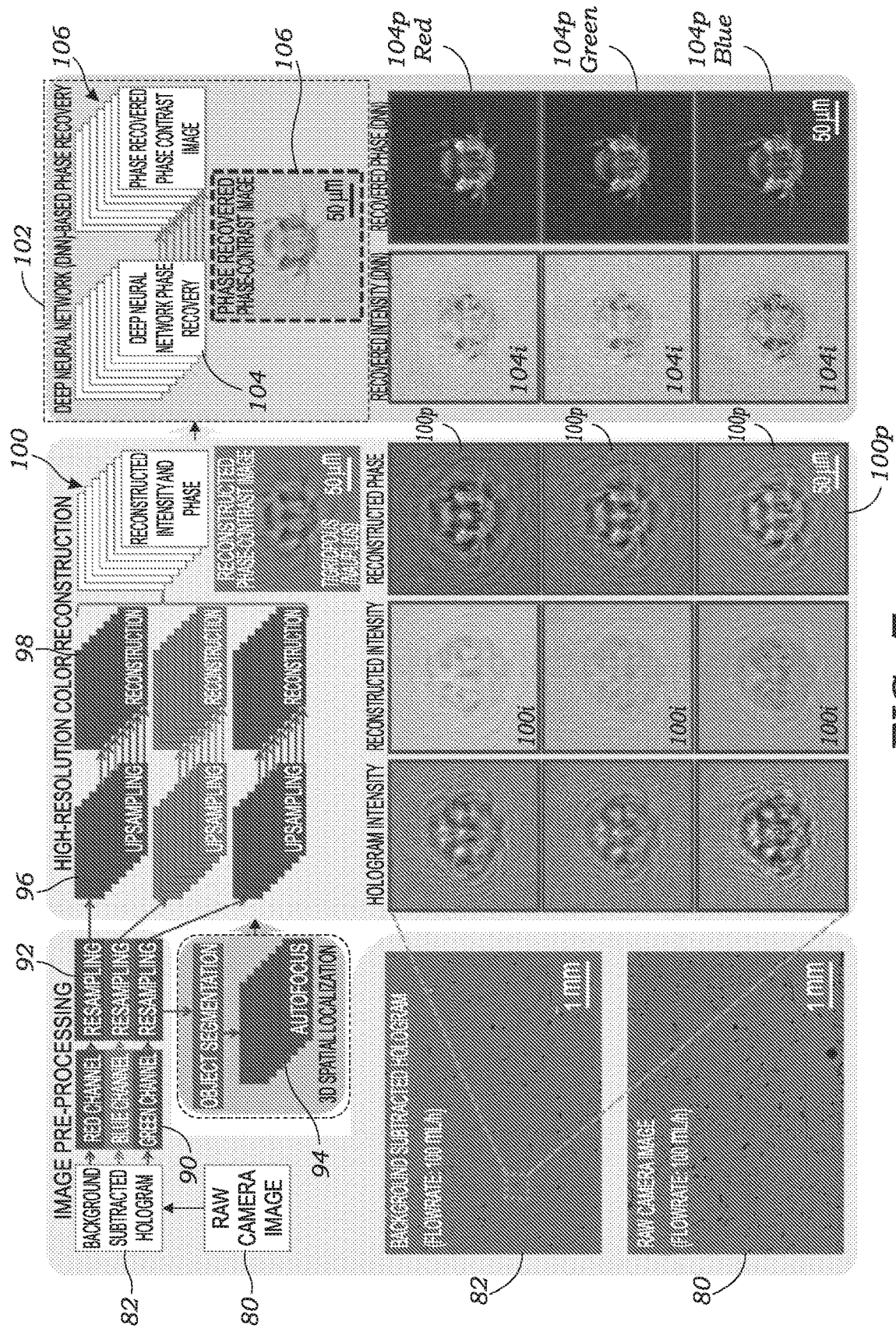
FIG. 7 schematically illustrates the operations of image pre-processing, high-resolution color reconstruction, and deep neural network (DNN)-based phase recovery. Image pre-processing involves background subtraction to eliminate artifacts, followed by resampling, object segmentation, and autofocusing to identify candidate objects of interest. High-resolution color reconstruction generates reconstructed intensity and phase images based on hologram images of objects. The reconstructed intensity and phase images for each color channel are input into a trained neural network to generate recovered intensity and/or phase images. The phase-recovered intensity and phase images in red, green and blue channels are fused to generate a final phase-contrast image per object (shown within the dashed black frame on the right).
Figure 8:
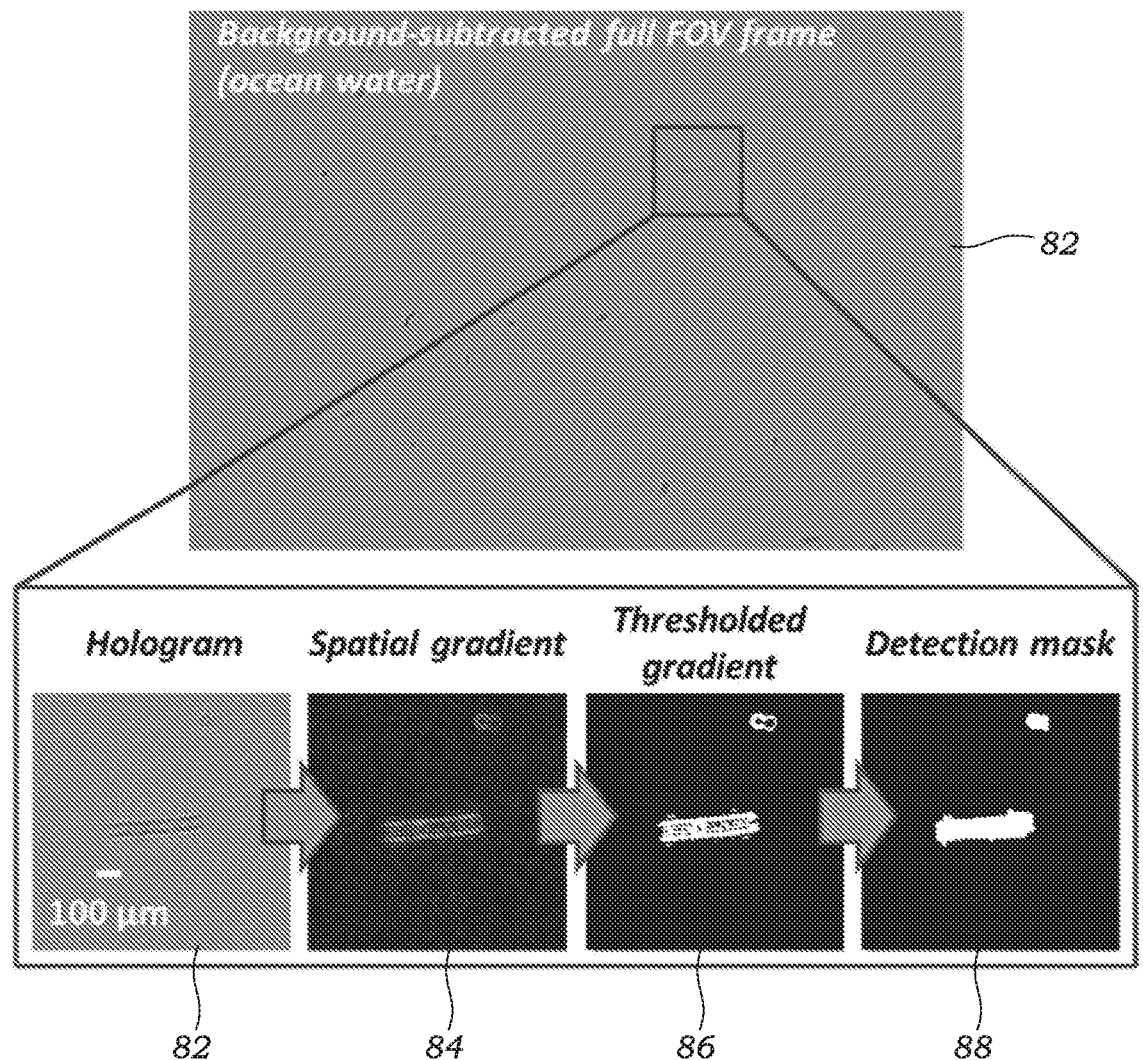
FIG. 8 illustrates a segmentation algorithm utilized by the image processing software used with the imaging flow cytometer device. The spatial gradient of the full field-of-view background-subtracted hologram is calculated to detect the rapidly oscillating holographic diffraction pattern of the object present in the image. The gradient is thresholded to create a binary image, and morphological closing is performed to obtain a single mask signature from each object. The center coordinates of the masks are calculated and used to segment the full field-of-view hologram into sub-holograms containing a single object (e.g., organism).

With reference to FIG. 7, for automatic detection and holographic reconstruction of the target objects 12 found in the continuously flowing water sample, the static objects 12 found in the raw full FOV image 80 (e.g., dust particles in the flow channel) need to be eliminated first. This is achieved by calculating a time-averaged image of the preceding~20 images 80, containing only the static objects, and subtracting it from the present raw hologram. To ensure appropriate reconstruction quality, the mean of this subtracted image is added back uniformly to the current frame. This yields a background-subtracted full FOV image 82 as seen in FIG. 7, in which only the holograms of the objects 12 newly introduced by the flow are present. These objects 12 are automatically detected and segmented from the full FOV for individual processing as seen in FIG. 8. The full FOV background-subtracted hologram 82 is first Gaussian-filtered as seen in operation 84 (FIG. 8) and converted into a binary image by hard-thresholding 86 with its statistical values (mean+1.5× standard deviation), which isolates the peaks of the holographic signatures created by the objects included in the FOV. The binary contours with an area of a few pixels are removed to reduce the misdetection events because of the sensor noise. A closing operation is performed in the generated binary image 88 to create a continuous patch for each object 12. The resulting binary contours represent the shapes and locations of the objects 12 appearing in the FOV, and their morphological information is used to filter each contour by certain desired criteria (e.g., major axis). The center coordinate of the filtered contour is used to segment its corresponding hologram. Not only is it feasible to extract all the objects 12 in the FOV but it is also possible to prioritize the segmentation of the objects 12 of interest for a specific goal by the approach. Using this, one can better utilize the computational resources of the computing device 24 and maintain real-time processing for denser samples.

After segmentation, the Bayer-patterned holograms are separated into three mono-color (i.e., red, green, and blue) holograms as seen in operation 90 (FIG. 7) corresponding to the illumination wavelengths. To fully utilize the spatial resolution of the optical system, the orientation of the Bayer-patterned green pixels is rotated by 45° to regularize their sampling grid. Concurrently, the red and blue mono-color holograms are upsampled by a factor of two, and a 45° rotation is applied to these upsampled holograms as seen in operation 92. Note that segmentation may be performed initially on the full FOV debayered image without any rotation applied (operation 92). After segmentation is complete, the original bayered, background subtracted hologram is then subject to the rotation operation 92. Holographic autofocusing using Tamura of complex gradient as seen in operation 94 is performed for each segmented object 12 using only a single mono-color hologram to accurately estimate the distance of the respective object 12 from the imaging plane of the image sensor 46. At this point, each object 12 within the flow is 3D localized (per FOV). The coordinates of each detected object 12 are then used in conjunction with the estimated flow profile from calculations, and the location of each object 12 is predicted at the next frame. If an object 12 is found at the predicted coordinates, it is flagged to be removed from the total count and processing workflow to avoid reconstructing and counting the same object 12 multiple times.

The next step is to maximize the resolution of the reconstruction by further upsampling the resampled holograms by a factor of four as seen in operation 96. Each color channel is then propagated to the obtained reconstruction distance by a wave propagation algorithm as seen in operation 98, and thus, it is brought into focus. In one particular embodiment, the wave propagation algorithm is an angular-spectrum based wave propagation algorithm. Details regarding the angular-spectrum based wave propagation algorithm may be found in Göröcs, Z. & Ozcan, A. On-Chip Biomedical Imaging. IEEE Rev. Biomed. Eng. 6, 29-46 (2013), which is incorporated herein by reference. The different refractive indices of the materials present in the optical path, namely the cover glass of the image sensor 46, the airgap between the image sensor 46 and the bottom of the microfluidic channel 14, the microfluidic channel 14, and the water or other fluid therein are taken into account respectively, by performing four (4) successive angular spectrum propagations each corresponding to the material and its respective thickness. The image sensor 46 cover glass, the airgap, and the bottom thickness of the microfluidic channel 14 are constant for each object 12, while the object's distance from the bottom of the microfluidic channel 14 varies, and is given by the result of the autofocus algorithm 94 performed on a single color as explained above. The slight incidence angle difference between the red, green, and blue emitters of the LED chip light source 50 is corrected by modifying the propagation kernel accordingly. To evaluate the resolution of the imaging flow cytometer device 10 for the objects 12 located inside the microfluidic channel 14, the flow channel was replaced with a 1951 Air Force test chart (see FIG. 16). Owing to the partially-coherent nature of the illumination, the resolution depends on the object-sensor distance; thus, it was measured by placing the test chart at various heights above the image sensor 46. The width of the smallest resolved line varied between 1.55 µm-1.95 µm depending on the height of the object 12, with 1.55 µm corresponding to the smallest resolvable feature for most flowing objects 12 imaged by the imaging flow cytometer device 10 during its regular operation.

These raw reconstructed phase and intensity images 100, which include both reconstructed intensity images 100i and reconstructed phase images 100p, however, are contaminated by self-interference and twin-image noise, which are characteristic of an in-line digital holographic imaging system, due to the loss of the phase information of the hologram at the plane of the image sensor 46. Thus, to achieve accurate image reconstruction without these artifacts, a deep learning-based digital holographic phase recovery method was employed, using a trained deep neural network 102 (e.g., convolutional neural network) (see FIGS. 7, 9A, 9B) that was pre-trained with various phase-recovered reconstructions of water-borne objects 12 captured with the imaging flow cytometer device 10. The phase-recovered ground truth or "gold standard" reconstructions may be obtained using, for example, multi-height images of the objects 12 in in which phase recovery is performed using multi-height phase recovery such as that disclosed in Rivenson et al., Phase recovery and holographic image reconstruction using deep learning in neural networks, Light Sci. Appl. 7, e17141 (2018), which is incorporated by reference herein. This enables automated and accurate acquisition of the spectral morphology of an object 12 without sacrificing the high-throughput operation of the imaging flow cytometer device 10, which otherwise would be very challenging as other existing phase recovery methods require static repetitive measurements and/or time-consuming iterative calculations which would not work for flowing objects 12.

The trained deep neural network 102 outputs phase recovered images 104 which include phase recovered intensity images 104i and phase recovered phase images 104p. The phase recovered intensity images 104i and phase recovered phase images 104p can be combined or merged to create phase recovered phase-contrast images 106 as seen in FIG. 7. FIG. 7 also shows in the panel of the trained deep neural network 102 as phase recovered phase-contrast image 106. For the visualization of transparent objects 12 such as plankton, the color phase-contrast image 106 based on the complex-valued reconstructions of the red, green, and blue channels assists in accurately resolving the fine features and internal structures of various water-borne microorganisms with a high color contrast (see e.g., FIG. 10).

Graphical User Interface (GUI)

A GUI 110 was used to operate the device (FIGS. 5 and 6) which the user interacts with via the display 26 of the computing device 24. Through this GUI 110, all the relevant measurement parameters can be specified, such as the liquid flow speed, the driving currents, the incidence angles for the red, green, and blue LEDs, the flash pulse duration, the camera sensor gain, etc. The GUI 110 gives a real time, full field-of-view reconstructed image at the center of the microfluidic channel 14 allowing visual inspection during the flow with and without background subtraction and displays the total number of the detected objects 12 in the current frame. The GUI 110 is also capable of visualizing up to twelve (12) segmented, autofocused, and reconstructed objects 12 in real time (or course more or less objects 12 could be displayed). The user can specify whether to digitally save any combination of the raw, background subtracted holograms, or reconstructed images (e.g., images 106). The GUI 110 can be also run in demo mode, allowing the analysis of previously captured image datasets, without the presence of the imaging flow cytometer device 10.

Sample Preparation and Analysis

The sampling protocol recommended by the CDPH (USA) for obtaining the ocean samples was followed. A plankton net was used with a diameter of 25 cm and vertical tows were performed with a total length of 15 m (5×3 m) from the end of the pier at each sampling location where a pier is present (Malibu, Santa Monica, Venice, Manhattan, and Redondo beaches in California, USA). There was no pier at the Point Dume so a horizontal tow was performed from the shoreline. The plankton net condensed the micro- and nano-plankton found in the ocean into a sample volume of ~250 mL, i.e., in this case a condensation ratio of ~3000×. 1 mL of the condensed sample was extracted and re-diluted with 50 mL of filtered ocean water its contents were imaged using the imaging flow cytometer device 10. The remaining samples were sent to the CDPH for subsequent analysis (used for comparison purposes). During the field tests, the same plankton net was used, but only performed one vertical tow was performed from a depth of 1.5 m at each measurement. 1 mL of the obtained sample was re-diluted by 20 mL of filtered ocean water. To conserve the battery power of the controlling computing device 24 (i.e., laptop), ~12 mL of this sample was imaged on-site. The imaging flow cytometer device 10 automatically detected and saved the reconstructed images 106 of all the detected plankton and provided the user real-time feedback on the total plankton count detected. Specific counting of *Pseudo-Nitzschia* was done manually by scanning through the dataset of the saved images and visually identifying *Pseudo-Nitzschia*.

In another embodiment and with reference to FIG. 17A, the flow cytometer imaging system 2 is used with a neural network classifier 114 that is configured to detect and count specific types of objects 12, e.g., specific types of microorganisms. In this alternatively embodiment, the trained deep neural network 102 previously described is substituted with a neural network classifier 114 that is trained, in one embodiment, to output a binary determination (i.e., yes/no) of whether the particular microorganism is of a particular type or species. For example, the neural network classifier 114 was used to detect and count various concentrations of *Giardia lamblia* cysts. The neural network classifier 114 trained for this purpose is a variant of the DenseNet-121 network described in Huang et al., Densely connected convolutional networks, In Proceedings of the IEEE conference on computer vision and pattern recognition, pp. 4700-4708 (2017), which is incorporated by reference.

Changes DenseNet-121 network include the omission of the batch-norm layer and use of a dropout of 0.3. The network optimizer of choice was adaptive moment estimation (ADAM). A total of 40000 *Giardia* images, and 40000 dirt particles images were used to train the neural network classifier 114. 8000 images of each category served as the validation set. Data augmentation techniques of image rotation and flipping were also employed to increase the variety of the sample images. The neural network classifier 114 was trained, and the subsequent decision was made on the reconstructed, but non-phase recovered phase and amplitude images. Just as in the case for the phase recovery trained neural network 102, the input of the neural network classifier 114 is also the reconstructed red, green, and blue intensity and phase images (i.e., images 100i, 100p in FIG. 7) (1024×1024×6 layers). Due to the pixel size of the imaging flow cytometer device 10, and the small size of the *Giardia* cysts, the center 256×256 area of every image is cropped as a first step. The entire network architecture can be seen in FIG. 17B.

The *Giardia lamblia* samples were prepared according to the EPA 1623.1 Method (EPA 1623.1, Section 7.12) by Wisconsin State Laboratory of Hygiene (Madison, Wis.) and the irradiation of samples was done by Waterborne Inc. (New Orleans, La.). The test samples have a *Giardia* cyst count of 10, 50, 100, and 500 respectively in the manufacturer's standard 1 ml buffer volume. These samples were re-diluted into 50 ml bottled water before being analyzed by the imaging flow cytometer device 10. The training of the neural network classifier 114 was performed on separate, high concentration *Giardia* samples (250000 cyst/ml), which allowed to generate a high number of *Giardia lamblia* images. Several non-spiked water samples were imaged to provide images of the typical dirt particles found in the buffer water.

After the training process was completed, the neural network classifier 114 with the best validation accuracy (97% for *Giardia*, and ~99.5% for dirt) was selected. Since even the high concentration *Giardia* samples contain some dirt in the buffer water which results in noisy labeling of the *Giardia* images, 100% validation accuracy for *Giardia* is not expected. After the neural network classifier 114 was trained the performance of the system 2 was tested using low concentration *Giardia* samples. The samples were imaged with a throughput of 100 ml/h, and, to allow fluorescence microscope comparison, the effluent of the imaging flow cytometer device 10 was collected and filtered onto a membrane. The filter membrane containing the *Giardia* cysts that flow through the imaging flow cytometer device 10 was treated with fluorescein labelled *Giardia* specific antibodies (product no. A300FLR-20X, Waterborne Inc.), and incubated overnight at 37° C. The fluorescently labeled cysts were manually counted using a benchtop microscope. The results show good agreement and are summarized in Table 2 below.

TABLE 2

| Number of *Giardia* the manufacturer's original sample | Fluorescence microscope count | Flow cytometer count using deep neural network classifier |
| --- | --- | --- |
| 500 | 243 | 239 |
| 500 | 234 | 207 |
| 100 | 56 | 55 |
| 100 | 56 | 59 |
| 100 | 31 | 41 |
| 50 | 43 | 36 |
| 50 | 17 | 16 |
| 50 | 33 | 28 |
| 10 | 3 | 4 |

Table 2 shows the performance of the imaging flow cytometer device 10 in detecting and automatically classifying *Giardia Lamblia* cysts. The 50 ml water samples were imaged at a 100 ml/h flow rate for ~30 minutes. In order to account for the cysts adhering to the manufacturer's sample container and subsequently lost during sample preparation, the sample was collected and filtered after it left the cytometer. The *Giardia* captured by the filters were fluorescently stained using *Giardia*-specific dye, and manually counted using a fluorescence microscope. The results show good agreement.

In another embodiment and with reference to FIG. 18, the flow cytometer imaging system 2 is used to compute the thickness of the object 12 or, alternatively, the refractive index distribution within an object 12. Computing the refractive index distribution within an object 12 such as a microorganism may be used to infer, for example specific biochemical states or properties that exist within the microorganism. As one specific example, the refractive index distribution may be computed for a microorganism 12 and used as a proxy to determine the chemical content of the organism. For example, the chemical content may include the lipid content of the organism. This may have significant potential for the identification and screening of microorganisms such as algae for biofuel applications.

The optical path difference is a measure of the distance travelled by the light inside the object 12 of interest (i.e., plankton) multiplied by the refractive index difference between the object 12 of interest and the surrounding medium. If the optical path length difference is defined as $\Delta L(x,y)$, then the phase distribution at the object plane at each wavelength can be written as $\phi_k(x,y)=2\pi \cdot \Delta L(x,y)/\lambda_k$. The phase of the wavefront is a $2\pi$ periodic measure, thus, in case of thicker objects and larger optical path lengths, phase wrapping can occur. This wrapped phase is $\phi_{k,wrapped}(x,y)=\phi_k(x,y)\pm 2N\pi$ where $-\pi<\phi_{k,wrapped}\leq\pi$ and N is an integer. These resulting wrapped phase maps $\{\phi_{k,wrapped}\}$ that are generated by the three phase-retrieved reconstructions at the three wavelengths can be processed, i.e. by an optimization algorithm, such as that disclosed in Luo et al., Pixel super-resolution using wavelength scanning, Light: Science & Applications (2016) 5, e16060, which is incorporated herein by reference, finds an optimum path length $\Delta L_{opt}(x,y)$ at each spatial point on the image (x,y) by minimizing a cost function that is defined as:

$$\sum_{k=1}^{K}\left|e^{j\phi_k(x,y)} - e^{j2\pi \cdot \Delta L_{opt}(x,y)/\lambda_k}\right|^2$$

In one implementation, in order to reduce the computation cost/time, one can define a search range of $[\Delta L_0-\min\{\lambda_k\}/2, \Delta L_0+\min\{\lambda_k\}/2]$, where $\Delta L_0$ is the initial guess of the optical path length:

$$\Delta L_0(x,y) = \frac{1}{2\pi \cdot (K-1)}\sum_{k=2}^{K}[\phi_k(x,y) - \phi_{k-1}(x,y)]\cdot\frac{\lambda_k \lambda_{k-1}}{\lambda_{k-1}-\lambda_k}$$

where the total number of wavelengths (K=3). Within this search interval, one can scan the values to find the optical path length $\Delta L_{opt}(x,y)$ that minimizes the cost function, resulting in the optical path difference. FIG. 18 shows an example for this process. The optical path difference is a measure which couples the refractive index distribution of the object 12 and the object's thickness together. If one knows the refractive index distribution of the object 12 the correct thickness can be calculated. Conversely, if one knows the thickness of the object 12 and the refractive index of the surrounding medium, it is possible to compute the refractive index distribution inside the object 12. In one possible application, obtaining the refractive index distribution inside a microorganism such as algae can be used to infer its lipid (or other chemical) content.

While embodiments of the present invention have been shown and described, various modifications may be made without departing from the scope of the present invention. For example, while the invention has been described largely in the context of a color imaging sensor some embodiments may use a monochrome image sensor. In addition, in some embodiments, only a single light source may be needed (not multiple colors). In addition, in some embodiments, a near-infrared light source may be used instead of multi-color LEDs. Likewise, the one or more light sources may operate in a continuous wave mode operation in one alternative embodiment with the image frames being acquired by the image sensor operating in a "pulsed mode" to capture similar image frames. The invention, therefore, should not be limited, except to the following claims, and their equivalents.

What is claimed is:

1. A portable imaging flow cytometer device comprising:
   a housing;
   at least one illumination source disposed in the housing and configured for pulsed or continuous wave operation;
   a microfluidic channel disposed in the housing and fluidically coupled to a source of fluid containing objects therein that is configured to flow through the microfluidic channel;
   an image sensor disposed adjacent to the microfluidic channel and disposed within an optical path that receives light from the at least one illumination source that passes through the microfluidic channel, the image sensor configured to capture a plurality of image frames containing raw hologram images of the objects passing through the microfluidic channel; and
   a computing device configured to receive the plurality of image frames generated by the image sensor, the computing device executing image processing software thereon to perform background subtraction and automatically detect and segment moving objects in the plurality of image frames and autofocus the moving objects to identify the height (z) location of the moving objects within the microfluidic channel.

2. The portable imaging flow cytometer device of claim 1, wherein the image sensor comprises a monochrome or color image sensor.

3. The portable imaging flow cytometer device of claim 2, wherein the at least one illumination source comprises multiple color LEDs and the multiple color LEDs are pulsed simultaneously.

4. The portable imaging flow cytometer device of claim 3, further comprising one or more bandpass filters configured to spectrally filter the light from the multiple color LEDs.

5. The portable imaging flow cytometer device of claim 3, further comprising a one or more capacitors disposed in the housing and configured to power the multiple color LEDs.

6. The portable imaging flow cytometer device of claim 2, wherein the at least one illumination source comprises multiple color LEDs and the multiple color LEDs emit light simultaneously for a continuous period of time.

7. The portable imaging flow cytometer device of claim 1, wherein the at least one illumination source comprises a near-infrared light source.

8. The portable imaging flow cytometer device of claim 1, further comprising a pump configured to pump the fluid through the microfluidic channel.

9. The portable imaging flow cytometer device of claim 1, wherein the optical path comprises a folded optical path.

10. The portable imaging flow cytometer device of claim 9, wherein the folded optical path comprises a mirror disposed in the housing.

11. The portable imaging flow cytometry device of claim 1, wherein the computing device is a local computing device and/or a remote computing device.

12. The portable image flow cytometry device of claim 1, wherein the image processing software is configured to reconstruct phase and/or intensity images of the moving objects for each LED color, wherein the reconstruction is performed using a wave propagation algorithm.

13. The portable image flow cytometry device of claim 12, wherein the image processing software further comprises a trained deep neural network, wherein the reconstructed phase and/or intensity images are input to the trained deep neural network that outputs a phase recovered intensity and/or phase image of the moving objects.

14. The portable image flow cytometry device of claim 13, wherein the trained deep neural network outputs a phase recovered and digitally-generated phase-contrast image of the moving objects.

15. The portable image flow cytometry device of claim 12, wherein the image processing software is configured to classify or identifying moving objects prior to reconstructing phase and/or intensity images of the moving objects.

16. The portable image flow cytometry device of claim 1, wherein the image processing software further comprises a trained deep neural network, wherein the reconstructed phase and/or intensity images are input to the trained deep neural network that automatically characterizes or identifies the type of the moving objects.

17. The portable image flow cytometry device of claim 1, wherein the image processing software is configured to count the moving objects and/or to classify the moving objects.

18. A method of imaging objects using the flow cytometry device of claim 1, comprising:
    obtaining a plurality of image frames while fluid containing objects is flowed through the microfluidic channel;
    performing a background subtraction operation using the image processing software to remove artifacts;
    identifying moving objects in the plurality of image frames after background subtraction with the image processing software;
    reconstructing intensity and phase images of the moving objects using the image processing software; and
    inputting the reconstructed intensity and phase images of the moving objects into a trained deep neural network executed by the image processing software, wherein the trained deep neural network outputs a phase recovered intensity and/or phase image of the moving objects or a phase recovered phase-contrast image of the moving objects.

19. The method of claim 18, wherein the fluid comprises water and the moving objects comprise microorganisms and wherein the trained deep neural network automatically characterizes or identifies the type of microorganism.

20. A method of imaging objects using the flow cytometry device of claim 1, comprising:
    obtaining a plurality of image frames while fluid containing objects is flowed through the microfluidic channel;

performing a background subtraction operation using the image processing software to remove artifacts;

identifying moving objects in the plurality of image frames after background subtraction with the image processing software;

reconstructing intensity and phase images of the moving objects using the image processing software; and inputting the reconstructed intensity and phase images of the moving objects into a trained deep neural network executed by the image processing software, wherein the trained deep neural network outputs a refractive index distribution inside the moving objects.

21. The method of claim 20, wherein the fluid comprises water and the moving objects comprise microorganisms and wherein refractive index distribution inside the moving objects is used as a proxy for chemical content within the microorganisms.

22. The method of claim 20, wherein the fluid comprises water and the moving objects comprise microorganisms and wherein refractive index distribution inside the moving objects is used as a proxy for lipid content within the microorganisms.

* * * * *